(12) United States Patent
Sakaguchi et al.

(10) Patent No.: US 8,062,887 B2
(45) Date of Patent: Nov. 22, 2011

(54) MONOCLONAL ANTIBODY SPECIFICALLY RECOGNIZING MODIFICATION SITE AFTER TRANSLATION OF P53 AND KIT FOR ASSAYING MODIFICATION SITE CONTAINING THE SAME

(75) Inventors: Kazuyasu Sakaguchi, Hokkaido (JP); Yoshiro Chuman, Hokkaido (JP); Yasuo Akebiyama, Fukuoka (JP); Miho Matsukizono, Fukuoka (JP); Maki Watanabe, Fukuoka (JP); Junichi Tsutsumi, Fukuoka (JP)

(73) Assignees: National University Corporation, Hokkaido University, Sapporo-Shi Hokkaido (JP); Genenet Co., Ltd., Fukuoka (JP)

(*) Notice: Subject to any disclaimer, the term of this patent is extended or adjusted under 35 U.S.C. 154(b) by 565 days.

(21) Appl. No.: 11/910,313

(22) PCT Filed: Mar. 31, 2006

(86) PCT No.: PCT/JP2006/306921
§ 371 (c)(1),
(2), (4) Date: Feb. 18, 2009

(87) PCT Pub. No.: WO2006/106957
PCT Pub. Date: Oct. 12, 2006

(65) Prior Publication Data
US 2009/0298700 A1 Dec. 3, 2009

(30) Foreign Application Priority Data
Apr. 1, 2005 (JP) ................. 2005-106130

(51) Int. Cl.
*C12N 5/12* (2006.01)
*C07K 16/18* (2006.01)

(52) U.S. Cl. ..... 435/330; 435/331; 435/344; 435/344.1; 530/300; 530/327; 530/350; 530/387.7; 530/387.9; 530/388.25; 530/388.8; 530/388.85

(58) Field of Classification Search .................. 530/300, 530/327, 350, 387.7, 387.9, 388.25, 388.8, 530/388.85; 435/330, 331, 344, 344.1
See application file for complete search history.

(56) References Cited

U.S. PATENT DOCUMENTS

| | | |
|---|---|---|
| 6,441,140 B1 | 8/2002 | Comb et al. |
| 6,884,597 B1 | 4/2005 | Taya et al. |
| 2005/0023912 A1 | 2/2005 | Lin et al. |
| 2006/0035296 A1 | 2/2006 | Taya et al. |

FOREIGN PATENT DOCUMENTS

| | | |
|---|---|---|
| EP | 1050581 | 11/2000 |
| EP | 1184665 | 3/2002 |
| JP | 2000-325086 | 11/2000 |
| JP | 2001-161398 | 6/2001 |
| JP | 2003-093056 | 4/2003 |
| WO | WO-9936532 | 7/1999 |
| WO | WO-9946574 | 9/1999 |
| WO | WO-0072011 | 11/2000 |
| WO | WO 2004/29622 | 4/2004 |

OTHER PUBLICATIONS

Craig et al., "Novel phosphorylation sites of human tumour suppressor protein p53 at Ser20 and Thr18 that disrupt the binding of mdm2 (mouse double minute 2) protein are modified in human cancers", Biochem J., Aug. 15, 1999; 133-141, vol. 342(Pt 1).

Otvos et al., "A monoclonal antibody to a multiphosphorylated, conformational epitope at the carboxy-terminus of p53", Biochim Biophys Acta., Sep. 16, 1998, 457-74, vol. 1404(3).

Sakaguchi et al., "DNA damage activates p53 through a phosphorylation-acetylation cascade", Genes Dev., Sep. 15, 1998, 2831-2841, vol. 12(18).

Taya, 53 no aphosphorylation to acetylation ni yoru Saibo Kino no Seigyo', Cell Technology, 2003, 29-33, vol. 22(1).

Wang et al., "Identification and Characterization of a Novel p300-mediated p53 Acetylation Site, Lysine 305", J. Biol. Chem., 25568-25576, 2003, vol. 278 (28).

International Preliminary Report on Patentability issued Oct. 3, 2007 during the Prosecution of International Application No. PCT/JP2006/306921.

Written Opinion issued Oct. 3, 2007 during the Prosecution of International Application No. PCT/JP2006/306921.

Banin et al., "Enhanced phosphorylation of p53 by ATM in response to DNA damage"; Science; Sep. 11, 1998; 1674-7; vol. 281 (5383).

Bulavin et al,. "Phosphorylation of human p53 by p38 kinase coordinates N-terminal phosphorylation and apoptosis in response to UV radiation"; The EMBO Journal; 1999; 6845-6854; vol. 18.

Chehab et al., "Chk2/hCds1 functions as a DNA damage checkpoint in G1 by stabilizing p53"; Genes Dev.; Feb. 1, 2000; 278-288; vol. 14(3).

Dumaz et al., "Serine 15 phosphorylation stimulates p53 transactivation but does not directly influence interaction with HDM2"; The EMBO Journal; 1999; 7002-7010; vol. 18.

Gu et al., "Activation of p53 sequence-specific DNA binding by acetylation of the p53 C-terminal domain."; Cell.; Aug. 22, 1997; 595-606; vol. 90(4).

(Continued)

*Primary Examiner* — Stephen Rawlings
(74) *Attorney, Agent, or Firm* — Fulbright & Jaworski L.L.P.

(57) ABSTRACT

The present invention provides a monoclonal antibody recognizing modification after translation of p53 in a manner specific to a modification site, an antibody microarray comprising the antibody immobilized on a substrate, etc. Disclosed is a monoclonal antibody which reacts specifically with a peptide consisting of an amino acid sequence of at least 6 consecutive amino acids containing a predetermined amino acid residue of the amino acid sequence represented by SEQ ID NO: 1, wherein the amino acid residue is phosphorylated or acetylated, or with a peptide having one to several arbitrary amino acids added to the above peptide, but does not react with the above peptide which is not phosphorylated or acetylated.

14 Claims, 13 Drawing Sheets

OTHER PUBLICATIONS

Higashimoto et al., "Human p53 Is Phosphorylated on Serines 6 and 9 in Response to DNA Damage-inducing Agents"; J. Biol. Chem.; Jul. 28, 2000; 23199-23203, vol. 275(30).

Lambert et al., "Phosphorylation of p53 Serine 15 Increases Interaction with CBP"; J Biol Chem; Dec. 4, 1998; 33048-33053; vol. 273(49).

Oda et al., "p53AIP1, a potential mediator of p53-dependent apoptosis, and its regulation by Ser-46-phosphorylated p53"; Cell; Sep. 15, 2000; 849-62; vol. 102(6).

Saito et al., "ATM mediates phosphorylation at multiple p53 sites, including Ser(46), in response to ionizing radiation"; J Biol Chem.; Apr. 12, 2002; 12491-4; vol. 277(15).

Sanchez-Prie et al., "A Role for the p38 Mitogen-activated Protein Kinase Pathway in the Transcriptional Activation of p53 on Genotoxic Stress by Chemotherapeutic Agents1"; Cancer Research; May 1, 2000; 2464-2472; vol. 60.

Shieh et al., "The human homologs of checkpoint kinases Chk1 and Cds1 (Chk2) phosphorylate p53 at multiple DNA damage-inducible sites"; Genes Dev.; Feb. 1, 2000; 289-300; vol. 14(3).

Tanaka et al., "A ribonucleotide reductase gene involved in a p53-dependent cell-cycle checkpoint for DNA damage"; Nature; 2000; 42-49; vol. 404.

Tibbetts et al., "A role for ATR in the DNA damage-induced phosphorylation of p53"; Genes Dev.; Jan. 15, 1999; 152-157; vol. 13(2).

Waterman et al., "ATM-dependent activation of p53 involves dephosphorylation and association with 14-3-3 proteins"; Nature Genetics; 1998; 175-178; vol. 19.

Yoichi Taya; "Structure of p53 and Sites for its Phosphorylation and Acetylation"; Experimental Medicine; 2001; 1050-1084; vol. 19(9), with English Translation thereof.

Office Action issued in Japanese Application No. 2007-511193 (and English translation theref), mailed May 27, 2011.

MONOCLONAL ANTIBODY SPECIFICALLY RECOGNIZING MODIFICATION SITE AFTER TRANSLATION OF P53 AND KIT FOR ASSAYING MODIFICATION SITE CONTAINING THE SAME

This Application is the National Phase Application of International Application No. PCT/JP2006/306921 filed Mar. 31, 2006, which claims priority to Patent Application in Japan No. 2005-106130, filed Apr. 1, 2005.

TECHNICAL FIELD

The present invention relates to a monoclonal antibody recognizing modification after translation of a cancer suppressor gene product p53 (herein after referred to sometimes as "p53" or "p53 protein") in a manner specific to a modification site, a hybridoma producing the monoclonal antibody, an antibody microarray and a kit for measuring modification after translation of p53 protein, and is particularly useful for study of the mechanism for regulation of expression of physical functions of p53, for development of anticancer agents and immunosuppressive agents, etc. The entire disclosure of Japanese Patent Application No. 2005-106130 filed on Apr. 1, 2005, with Japanese Patent Office, including specification, claims, drawings and abstract, is incorporated herein by reference in its entirety.

BACKGROUND ART p53 is a transcription factor that is activated by a variety of cell stresses and binds to a specific DNA sequence of a target gene, to control its transcriptional activity. p53 exhibits various physiological functions such as DNA repair, cell cycle arrest and apoptosis induction through the regulation of expression of a plurality of target genes.

p53 is usually maintained at a low level in a cell, and when the cell receives cellular stresses such as irradiation with radiations, irradiation with ultra violet ray, DNA damage by anticancer agents such as adriamycin, heat shock, osmotic shock and low-oxygen shock, p53 is stabilized and accumulated in the nucleus and activated as a transcription factor. Activated p53 induces the expression of genes such as p21$^{WAF1}$ involved in checkpoint control, DDB2 and p53R2 involved in DNA repair, and BAX and p53AIP1 involved in apoptosis.

Recently, it has been revealed that modification after translations to p53, such as phosphorylation and acetylation, are profoundly involved in the regulation of expression of these physiological functions.

When minor DNA damage is caused by exposure to X-ray or UV ray, ATM (Ataxia Telangiectasia Mutated) and ATR (Ataxia Telangiectasia Related) are activated to phosphorylate Chk1 and Chk2 downstream therefrom, and Chk1 and Chk2 in turn phosphorylate serine at position 20 (herein after referred to sometimes as "Ser20") in p53 and inhibit association of p53 with MDM2, thereby ubiquitinating p53 to prevent it from being decomposed with proteasomes, thus stabilizing p53. Serine at position 15 (herein after referred to sometimes as "Ser15") in p53 is directly phosphorylated by ATM and ATR, thereby inhibiting the binding of MDM2 protein to p53, thus stabilizing and activating p53. The stabilized and activated p53 binds to a promoter of a G1 arrest period-related gene p21$^{WAF1}$ or to a promoter of a DNA repair-related gene p53R2, to induce its expression.

When severe DNA damage is caused, Ser46 kinase is activated to phosphorylate serine at position 46 (herein after referred to sometimes as "Ser46") in activated p53. The p53 phosphorylated at Ser46 binds to a promoter of p53AIP1 gene to induce expression of the p53AIP1 gene, thereby activating a p53-dependent apoptosis pathway to kill cells through apoptosis. Further, it is reported that p38MAPK activated by irradiation with ultra violet ray or with an anticancer drug phosphorylates serine at 33 position (herein after referred to sometimes as "Ser33") in p53, thereby participating in p53-dependent apoptosis. It is also reported that both serine at position 376 (herein after referred to sometimes as "Ser376") and serine at position 378 (herein after referred to sometimes as "Ser378") located in the C-terminal region of p53 have been phosphorylated in a usual state in a cell, but when the cell undergoes DNA damage by irradiation with radiations, the phosphorylated state of Ser376 is maintained while Ser378 is dephosphorylated.

The expression of physiological functions of p53 is also controlled by acetylation of p53. p53 controls transcription of its target genes through interaction with transcriptional coactivators (cofactors) among which P300/CBP, PCAF, etc. have a histone acetyltransferase (HAT) activity. p53 interacts with such HATs to promote the histone acetylation of the target genes, while p53 itself is also acetylated by which lysine residues at positions 320, 373 and 382 (herein after referred to sometimes as "Lys320", "Lys373", and "Lys382" respectively) in the C terminal of p53. PCAF/GCN5 specifically acetylates Lys320, and p300/CBP specifically acetylates Lys373 and Lys382. When p53 is acetylated, its ability to specifically bind to DNA is enhanced. An estimated reason for this is that the positive charge of the C-terminal is neutralized by acetylation, which results in a structural change in p53 to cause exposure of a DNA domain of p53. There is also proposed a model in which the N-terminal is phosphorylated upon activation by DNA damage etc., followed by binding HAT such as p300/CBP to the N-terminal and acetylating the C-terminal.

Human p53 protein is composed of 393 amino acid residues and divided roughly into 3 regions, that is, (i) 1 to 100 amino acid residues in a transcriptional activation domain and a proline-enriched domain, (ii) 100 to 300 amino acid residues in a sequence-specific DNA-binding domain, and (iii) 300 to 393 amino acid residues in a tetramer-forming domain and a basicity-regulating domain, and it has been previously revealed that 7 phosphorylated sites (that is, Ser15, Ser20, Ser33, serine at position 37 (herein after referred to sometimes as "Ser37"), Ser46, threonine at position 81 (herein after referred to sometimes as "Thr81"), and serine at position 90 (herein after referred to sometimes as "Ser90")) are present in the N-terminal region containing the transcriptional activation domain and the proline-enriched domain, and also that 5 phosphorylated sites (that is, serine at position 315 (herein after referred to sometimes as "Ser315"), serine at position 371 (herein after referred to sometimes as "Ser371"), Ser376, Ser378 and serine at position 392 (herein after referred to sometimes as "Ser392")) and 3 acetylated sites (that is, Lys320, Lys373, Lys382) are present in the C-terminal region.

In the p53 gene whose mutations are detected most frequently in human cancers, most of the mutations are concentrated in DNA binding regions. This suggests that canceration by p53 mutation is attributable to an abnormality in its expression regulatory system. Accordingly, it is essential to elucidate the mechanism for regulation of expression of physiological functions by the above-mentioned modification after translation of p53, in order to elucidate the mechanism of canceration via p53 mutation, and there is strong demand for development of tools (for example antibodies) and measurement methods capable of detecting or quantifying phosphorylation and/or acetylation in specific sites of p53.

In view of such demand, methods of measuring the enzyme activities of Chk1, Chk2, ATM, ATR, and DNP-PK have been proposed, and p53 modification sites after translation specific polyclonal antibodies used in these methods are known (patent literature 1 to 5 and non-patent literature 1 to 18).

Patent Literature 1: International Publication No. 99/36532

Patent Literature 2: JP-A 2000-325086

Patent Literature 3: JP-A 2001-161398

Patent Literature 4: Japanese Patent Application Laid-Open (JP-A) No. 2002-524092

Patent Literature 5: JP-A 2003-93056

Non-Patent Literature 1: Tanaka, H et al.: Nature, 404:42-49, 2000

Non-Patent Literature 2: Oda, K. et al.: Cell 102:849-862, 2000

Non-Patent Literature 3: Chehab, N. H. et al.: Gene Dev., 14:278-288, 2000

Non-Patent Literature 4: Shieh, S. Y. et al.: Gene Dev., 14:289-300, 2000

Non-Patent Literature 5: Banin, S. et al.: Science, 281: 1674-1677, 1998

Non-Patent Literature 6: Tibbetts, R. S. et al.: Gene Dev., 13:152-157, 1999

Non-Patent Literature 7: Dumaz, N. and Meek, D. W.: EMBO J., 18:7002-7010, 1999

Non-Patent Literature 8: Bulavin, D. V. et al., EMBO J., 18:6845-6854, 1999

Non-Patent Literature 9: Sanchez-Prieto, R.: Cancer Res., 60:2464-2472, 2000

Non-Patent Literature 10: Waterman, M. J. F. et al.: Nature Genet., 19:175-178, 1998

Non-Patent Literature 11: Gu, W. and Roeder, R. G.: Cell, 90:595-606, 1997

Non-Patent Literature 12: Sakaguchi, K. et al.: Gene Dev., 12:2831-2841, 1998

Non-Patent Literature 13: Lambert, P. F. et al.: J. Biol. Chem., 273:33048-33053, 1998

Non-Patent Literature 14: Experimental Medicine, edited by Yoichi Taya, 19 (No. 9):1050-1084, 2001

Non-Patent Literature 15: 2001; Yoichi Taya, Cell Engineering, Vol. 22, No. 1, p 29-33, 2003

Non-Patent Literature 16: J Biol Chem. 2000 Jul. 28; 275 (30):23199-23203

Non-Patent Literature 17: J Biol Chem. 2002 Apr. 12; 277(15):12491-12494

Non-Patent Literature 18: J Biol Chem. 2003 Jul. 11; 278 (28):25568-25576.

DISCLOSURE OF THE INVENTION

However, the conventional methods and polyclonal antibodies cannot be said to be satisfactory in respect of specificity for modification sites after translation, and there is demand for development of tools capable of parallel and independent detection and quantification of modified states in modification sites after translation of p53. Inhuman 53, there are not only the above-mentioned modification sites after translation but also 4 phosphorylated sites (that is, serine residue at position 6 (herein after referred to sometimes as "Ser6"), serine residue at position 9 (herein after referred to sometimes as "Ser9"), threonine residue at position 18 (herein after referred to sometimes as "Thr18") and threonine residue at position 55 (herein after referred to sometimes as "Thr55")), as well as 4 acetylated sites (that is, lysine at position 305 (herein after referred to sometimes as "Lys305"), lysine at position 370 (herein after referred to sometimes as "Lys370"), lysine at position 372 (herein after referred to sometimes as "Lys372"), and lysine at position 381 (herein after referred to sometimes as "Lys381")), so the regulation of expression of physiological functions by the phosphorylation/dephosphorylation and acetylation/deacetylation of p53 cannot be sufficiently elucidated in the conventional art described above. Further, p53 undergoes an intramolecular change via a plurality of modification after translation signals and is thus expected to interact not only intramolecularly but also among p53 molecules, so there is strong demand for development of tools capable of simultaneous and comprehensive detection and quantification of modified states in a plurality of modification sites after translation of p53.

Accordingly, the object of the present invention is to provide a monoclonal antibody specifically recognizing modification after translation of p53 in a manner specific to a modification site, an antibody microarray having the antibody immobilized on a substrate, etc.

The present inventors made extensive study to achieve the object, and as a result, they found that the object of the invention can be achieved by the following monoclonal antibody, antibody microarray etc., and the present invention was thereby arrived at.

That is, the present invention relates to:
(1) a monoclonal antibody reacting specifically with the following peptide (a), (b) or (c) but not reacting with the above peptide which is not phosphorylated or acetylated, (a) a peptide consisting of an amino acid sequence of at least 6 consecutive amino acids containing an amino acid residue at position 6, position 9, position 15, position 18, position 20, position 33, position 37, position 46, position 55, position 81, position 90, position 315, position 371, position 376, position 378 or position 392 in an amino acid sequence represented by SEQ ID NO: 1, wherein the amino acid residue is phosphorylated, (b) a peptide consisting of an amino acid sequence of at least 6 consecutive amino acids containing an amino acid residue at position 305, position 320, position 370, position 372, position 373, position 381 or position 382 in an amino acid sequence represented by SEQ ID NO: 1, wherein the amino acid residue is acetylated, or (c) a peptide having one to several arbitrary amino acids added to the peptide (a) or (b);

(2) the monoclonal antibody according to the above-mentioned (1), wherein the peptide (a) is a peptide consisting of an amino acid represented by SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or SEQ ID NO: 17, and the peptide (b) is a peptide consisting of an amino acid represented by SEQ ID NO: 18, SEQ ID NO: 19, SEQ ID NO: 20, SEQ ID NO: 21, SEQ ID NO: 22, SEQ ID NO: 23 or SEQ ID NO: 24;

(3) the monoclonal antibody according to the above-mentioned (2), which is produced by a hybridoma denoted by P53No. 18 4B (FERM ABP-10561), P53No. 17 16B (FERM AP-20478), P53No. 23 1C (FERM AP-20479), P53No. 5 16A (FERM ABP-10562), P53No. 10 6A (FERM ABP-10563) or P53No. 2 20G (FERM AP-20480), more preferably P53No. 18 4B (FERM ABP-10561), P53No. 5 16A (FERM ABP-10562), or P53No. 10 6A (FERM ABP-10563);

(4) the monoclonal antibody according to the above-mentioned (2), which is produced by a hybridoma denoted by:
P53No. 3 3Bc (FERM ABP-10576),
P53No. 4 13C (FERM ABP-10577),
P53No. 11 7C (FERM ABP-10578),
P53No. 12 1A (FERM ABP-10579),
P53No. 22 11B (FERM ABP-10580) or
P53No. 23 1A (FERM ABP-10581);
(5) a hybridoma producing the monoclonal antibody of any of the above-mentioned (1) to (4);
(6) the hybridoma according to the above-mentioned (5), which is denoted by P53No. 18 4B (FERM ABP-10561), P53No. 17 16B (FERM AP-20478), P53No. 23 1C (FERM AP-20479), P53No. 5 16A (FERM ABP-10562), P53No. 10 6A (FERM ABP-10563) or P53No. 2 20G (FERM AP-20480);
(7) the hybridoma according to the above-mentioned (5), which is denoted by:
P53No. 3 3Bc (FERM ABP-10576),
P53No. 4 13C (FERM ABP-10577),
P53No. 11 7C (FERM ABP-10578),
P53No. 12 1A (FERM ABP-10579),
P53No. 22 11B (FERM ABP-10580) or
P53No, 23 1A (FERM ABP-10581);
(8) an antibody microarray comprising the monoclonal antibody of any of the above-mentioned (1) to (4) immobilized on a substrate;
(9) a kit for measuring a modification state after translation of p53 protein, which comprises the monoclonal antibody of any of the above-mentioned (1) to (4) or the antibody microarray of the above-mentioned (8); and
(10) a method for measuring a modification state after translation of p53 protein, which comprises using the monoclonal antibody of any of the above-mentioned (1) to (4) or the antibody microarray of the above-mentioned (8).

The monoclonal antibody of the present invention specifically recognizes and binds to a modified amino acid residue, or an amino acid residue in the vicinity thereof, in a modification site after translation of p53, and when the amino acid residue in a modification site after translation has not undergone modification, the monoclonal antibody does not bind thereto. Accordingly, the monoclonal antibody can be used in independent and parallel detection and quantification of modified states in a plurality of modification sites after translation of p53 and is extremely useful in p53 study and cancer diagnosis. Particularly, the phosphorylation of p53 leads to suppression of inactivation of p53 and to signal enhancement and is regulated by 2 cascades including the secondary activation of mutually dependent modification enzymes and of intramolecular modification of p53 and the integration of signals from various stresses. Since these mutually dependent cascades in modified sites are anticipated to have been established, the antibody microarray and kit of the invention which can simultaneously and comprehensively detect phosphorylated states in a plurality of modification sites after translation of p53 are useful. The antibody microarray of the present invention can be used in simultaneous and comprehensive detection of modified states in a plurality of modification sites after translation on p53 and can serve as a very useful tool not only for elucidation of the mechanism for p53 suppression of malignant transformation but also for cancer diagnosis or therapy. The measurement kit and measurement method of the present invention can be used in easy and rapid detection and quantification of modification sites after translation of p53 and are extremely useful in p53 study and cancer diagnosis/therapy.

BEST MODE FOR CARRYING OUT THE INVENTION

Figure 1:
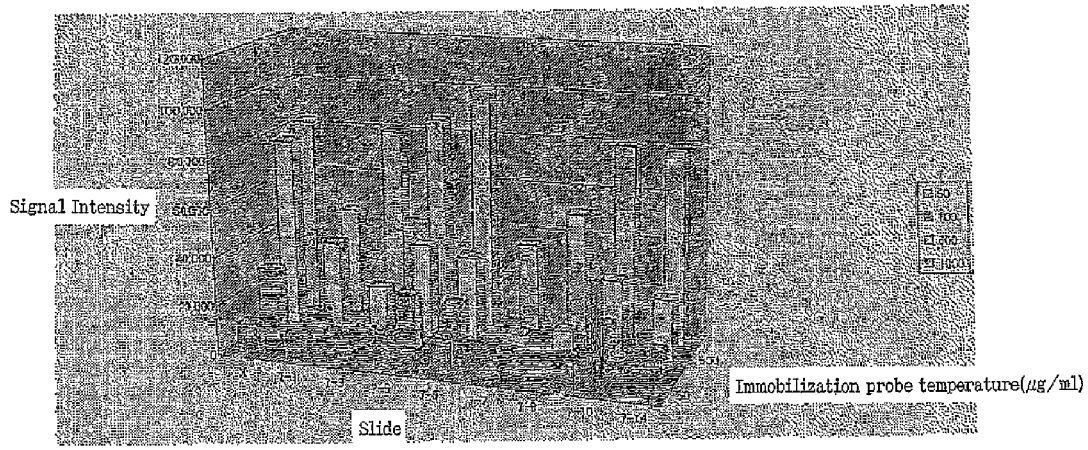
FIG. 1 is a graph showing signal intensities of DO-1 antibody spotted on various coating slide glasses.

Hereinafter, the denotation of amino acids and (poly)peptides in the invention by their abbreviations follows IUPAC-IUB regulations (IUPAC-ICB Communication on Biological Nomenclature, Eur. J. Biochem., 138:9 (1984)) and "Guidelines for Preparation of Specification Etc. Containing Nucleotide Sequence or Amino Acid Sequence" (compiled by Japanese Patent Office).

In the present invention, "(poly)peptide" refers to a compound having two or more amino acids bound via a peptide linkage, which may has any chain length. Accordingly, the "(poly)peptide" referred to in the present invention also encompasses a protein. The "protein" and "(poly)peptide" in the present invention encompasses not only "protein" and "(poly)peptide" represented by a specific amino sequence, but also its homologs (including splice variants), mutants, derivatives, mature bodies and amino acid-modified bodies insofar as they have biological functions equivalent thereto. The homologs can be exemplified by proteins of other biological species, corresponding to the human protein, and such proteins can be identified deductively from the nucleotide sequence of their gene. The mutants include mutants which occur or does not occur naturally and mutants having an amino acid sequence modified artificially by addition, substitution, addition and insertion. The mutants can include those having at least 85%, preferably 90% and more preferably 95% homology with the intact protein or (poly)peptide.

In the present invention, the term "translation" refers to a process wherein information of mRNA generated through transcription from genomic DNA (or RNA in some cases) is read and converted into an amino acid sequence on a ribosome to form a protein. The "modification after translation" refers to a process wherein the protein formed through translation further undergoes various modifications, depending on the role and activity of the protein, and specific examples include modifications to amino acid residues, such as cleavage (processing) of a peptide chain by a specific protease, phosphorylation, acetylation, methylation, adenylation, ADP ribosylation, and sugar chain addition. Unless otherwise specified, the "p53 modified after translation" in the present invention refers to phosphorylated and/or acetylated p53 after translation, and unless otherwise specified, the "modified (poly)peptide" and "unmodified (poly)peptide" refer to a phosphorylated and/or acetylated (poly)peptide and a (poly) peptide not phosphorylated or acetylated, respectively.

Human p53 consists of 393 amino acids, and its amino acid sequence is shown in SEQ ID NO: 1. Unless otherwise specified, the modification site after translation of p53 in the present invention refers to amino acid residues capable of modification after translation (phosphorylation or acetylation) in vivo or in vitro with kinases such as Chk1, Chk2, ATM, ATR, Ser46 kinase, p38MAPK, PKC and CKII and HATs such as p300/CBP, PCAF and GCN5, and specifically the phosphorylation sites of p53 can include residues in human p53, such as serine at position 6, serine at position 9, serine at position 15, threonine at position 18, serine at position 20, serine at position 33, serine at position 37, serine at position 46, threonine at position 55, threonine at position 81, serine at position 90, serine at position 315, serine at position 371, serine at position 376, serine at position 378 and serine at position 392, and the acetylation sites can include residues in human p53, such as lysine at position 305, lysine at position 320, lysine at position 370, lysine at position 372, lysine at position 373, lysine at position 381 and lysine at position 382.

The monoclonal antibody of the present invention is characterized by reacting specifically with the following peptide (a), (b) or (c) but not reacting with the above peptide which is not phosphorylated or acetylated, (a) a peptide consisting of an amino acid sequence of at least 6 consecutive amino acids containing an amino acid residue at position 6, position 9, position 15, position 18, position 20, position 33, position 37, position 46, position 55, position 81, position 90, position 315, position 371, position 376, position 378 or position 392 in an amino acid sequence represented by SEQ ID NO: 1, wherein the amino acid residue is phosphorylated;

(b) a peptide consisting of an amino acid sequence of at least 6 consecutive amino acids containing an amino acid residue at position 305, position 320, position 370, position 372, position 373, position 381 or position 382 in an amino acid sequence represented by SEQ ID NO: 1, wherein the amino acid residue is acetylated; or (c) a peptide having one to several arbitrary amino acids added to, substituted on, or inserted into, the peptide (a) or (b), provided that these modifications exclude the substitution of phosphorylated amino acid residues or acetylated amino acid residues with amino acids.

The monoclonal antibody of the present invention reacts specifically with any of the peptides (a), (b) and (c), but does not react with the above peptides which are not modified. That is, the monoclonal antibody of the invention recognizes and binds to a modification site after translation of amino acid residue, or an amino acid residue in the vicinity thereof, in p53, but does not bind to an unmodified amino acid residues in a modification site after translation. This specificity enables independent and parallel detection and quantification of modifications (phosphorylation or acetylation) in a plurality of modification sites after translation of p53 protein.

The peptide (a) is a peptide consisting of a consecutive amino acid sequence containing phosphorylated Ser6, phosphorylated Ser9, phosphorylated Ser15, phosphorylated Thr18, phosphorylated Ser20, phosphorylated Ser33, phosphorylated Ser37, phosphorylated Ser46, phosphorylated Thr55, phosphorylated Thr81, phosphorylated Ser90, phosphorylated Ser315, phosphorylated Ser371, phosphorylated Ser376, phosphorylated Ser378 or phosphorylated Ser392 in human p53, preferably a phosphorylated peptide containing phosphorylated Ser6, phosphorylated Ser9, phosphorylated Ser20, phosphorylated Thr55, phosphorylated Thr81, phosphorylated Ser90, phosphorylated Ser315, phosphorylated Ser371, phosphorylated Ser376, or phosphorylated Ser378, more preferably a phosphorylated peptide containing phosphorylated Ser9, phosphorylated Ser20 or phosphorylated Thr81. Its length is from 6 amino acids to the full length, more preferably 6 to 20 amino acids, still more preferably 6 to 14 amino acids.

The peptide (a) is more preferably a peptide consisting of an amino acid sequence represented by MEEPQS$^{(P)}$DPSVEP (SEQ ID NO: 2), PQSDPS$^{(P)}$VEPPLS (SEQ ID NO: 3), EPPLS$^{(P)}$QETFSDL (SEQ ID NO: 4), PLSQET$^{(P)}$FSDLWK (SEQ ID NO: 5), SQETFS$^{(P)}$DLWKLL (SEQ ID NO: 6), PENNVLS$^{(P)}$PLPSQA (SEQ ID NO: 7), LSPLPS$^{(P)}$QAMDDL (SEQ ID NO: 8), DDLMLS$^{(P)}$PDDIEQ (SEQ ID NO: 9), IEQWFT$^{(P)}$EDPGPD (SEQ ID NO: 10), APAAPT$^{(P)}$PAAPAP (SEQ ID NO: 11), PAPAPS$^{(P)}$WPLSSS (SEQ ID NO: 12), NNTSSS$^{(P)}$PQPKKK (SEQ ID NO: 13), SSHLKS$^{(P)}$KKGQST (SEQ ID NO: 14), SKKGQS$^{(P)}$TSRHKK (SEQ ID NO: 15), KKGQSTS$^{(P)}$RHKKLMF (SEQ ID NO: 16), or FKTEGPDS$^{(P)}$D (SEQ ID NO: 17), still more preferably a peptide consisting of an amino acid sequence represented by MEEPQS$^{(P)}$DPSVEP (SEQ ID NO: 2), PQSDPS$^{(P)}$VEPPLS (SEQ ID NO: 3), SQETFS$^{(P)}$DLWKLL (SEQ ID NO: 6), IEQWFT$^{(P)}$EDPGPD (SEQ ID NO: 10), APAAPT$^{(P)}$PAAPAP (SEQ ID NO: 11), PAPAPS$^{(P)}$WPLSSS (SEQ ID NO: 12), NNTSSS$^{(P)}$PQPKKK (SEQ ID NO: 13), SSHLKS$^{(P)}$KKGQST (SEQ ID NO: 14), SKKGQS$^{(P)}$TSRHKK (SEQ ID NO: 15), or KKGQSTS$^{(P)}$RHKKLMF (SEQ ID NO: 16), further more preferably a peptide consisting of an amino acid sequence represented by PQSDPS$^{(P)}$VEPPLS (SEQ ID NO: 3), SQETFS$^{(P)}$DLWKLL (SEQ ID NO: 6), or APAAPT$^{(P)}$PAAPAP (SEQ ID NO: 11). In the above amino acid sequences, S$^{(P)}$ represents phosphorylated serine, and T$^{(P)}$ represents phosphorylated threonine.

The peptide (b) is a peptide consisting of a consecutive amino acid sequence containing acetylated Lys305, acetylated Lys320, acetylated Lys370, acetylated Lys372, acetylated Lys373, acetylated Lys381 or acetylated Lys382 in human p53, preferably an acetylated peptide containing acetylated Lys305, acetylated Lys320, acetylated Lys370, acetylated Lys372, or acetylated Lys381, more preferably an acetylated peptide containing acetylated Lys305 or acetylated Lys320. Its length is from 6 amino acids to the full length, more preferably 6 to 20 amino acids, still more preferably 6 to 14 amino acids.

The peptide (b) is more preferably a peptide consisting of an amino acid sequence represented by PPGSTK$^{(Ac)}$RALPNN (SEQ ID NO: 18), SPQPKK$^{(Ac)}$KPLDG (SEQ ID NO: 19), HSSHLK$^{(Ac)}$SKKGQ (SEQ ID NO: 20), SHLKSK$^{(Ac)}$KGQST (SEQ ID NO: 21), HLKSKK$^{(Ac)}$GQSTS (SEQ ID NO: 22), STSRHK$^{(Ac)}$KLMFK (SEQ ID NO: 23), or TSRHKK$^{(Ac)}$LMFKT (SEQ ID NO: 24), still more preferably a peptide consisting of an amino acid sequence represented by PPGSTK$^{(Ac)}$RALPNN (SEQ ID NO: 18), SPQPKK$^{(Ac)}$KPLDG (SEQ ID NO: 19), HSSHLK$^{(Ac)}$SKKGQ (SEQ ID NO: 20), SHLKSK$^{(Ac)}$KGQST (SEQ ID NO: 21), or STSRHK$^{(Ac)}$KLMFK (SEQ ID NO: 23), further more preferably a peptide consisting of an amino acid sequence represented by PPGSTK$^{(Ac)}$RALPNN (SEQ ID NO: 18) or SPQP-KK$^{(Ac)}$KPLDG (SEQ ID NO: 19). In the above amino acid sequences, K$^{(Ac)}$ represents acetylated lysine.

The peptide (c) can include a peptide having 1 to 5 arbitrary amino acids added to the peptide (a) or (b), a peptide having 1 to 5 arbitrary amino acids substituted on the peptide (a) or (b) (provided that in the peptide (a) or (b), the substitution of a phosphorylated serine residues, a phosphorylated threonine residue or an acetylated lysine residue with another amino acid is excluded), and a peptide having 1 to 5 arbitrary amino acids inserted into the peptide (a) or (b), preferably a peptide having 1 or 2 amino acids added to, substituted on, or inserted into, the peptide (a) or (b).

The monoclonal antibody of the present invention includes antibody fragments such as Fv, Fab, F (ab')$_2$, scFv and dsFv, and its biological species or production method is not particularly limited. The monoclonal antibody of the present invention also includes those antibodies such as hybrid antibodies, modified antibodies, chimeric antibodies and humanized antibodies which are produced without using hybridomas (for example, recombinant antibodies produced by transformants transformed with an expression vector containing the antibody gene). The antibody fragments can be obtained for example by treating the monoclonal antibody of the present invention with proteases such as papain and pepsin.

The monoclonal antibody of the present invention can be labeled arbitrarily with a suitable labeling substance, depending on its intended use. The labeling substance is selected suitably depending on the intended use; for example, it is possible to use enzymes such as horseradish peroxidase, β-D-galactosidase, alkali phosphatase, glucose-6-dehydrogenase and acetylcholine esterase, fluorescent substances such as Cy3, Cy5 and fluorescein isothiocyanate (FITC), radioisotopes such as $^{125}$I, $^{131}$I, $^{14}$C, $^{3}$H, $^{32}$P and $^{35}$S, luminescent substances such as luminol, luminol derivatives and luciferin, biotin, lanthanide elements etc.

Instead of labeling the antibody of the present invention, a secondary antibody or protein A which specifically binds to the antibody of the present invention may be labeled with the labeling substance. When the enzyme is used as a labeling substance, a substrate, a coloring agent etc. may be used for measuring its activity. For example, when horseradish peroxidase is used as the enzyme, $H_2O_2$ is used as the substrate, 2,2'-azino-di-[3-ethylbenzthiazolinesulfonate]ammonium salt (ABTS), 5-aminosalicylic acid, orthophenylenediamine (OPD) or the like is used as the coloring agent; when alkali phosphatase is used as the enzyme, orthonitrophenyl phosphate or the like is used as the substrate; and when β-D-galactosidase is used as the enzyme, fluorescein-di-(β-D-galactopyranoside) or the like can be used as the substrate.

The monoclonal antibody of the present invention can be obtained by using any of the peptides (a), (b) and (c) as antigen. To minimize production of antibodies against portions not containing a modified amino acid, a peptide wherein the modified amino acid residue is positioned in the center of the peptide is preferably used as the antigen. A peptide having cysteine added to the N- or C-terminal of the peptide may be used for bonding a carrier protein described later to the peptide, or a peptide having an acetyl group introduced into an N-terminal α-amino group may be used to protect the N-terminal α-amino group.

As the method for preparation of the antigen, any methods known in the art can be used; for example, the antigen can be prepared by a known peptide synthesis method of using a peptide automatic synthesizer or by culturing a transformant containing a DNA encoding the antigen.

As the known peptide synthesis method of using a peptide automatic synthesizer, it is possible to use either a solid-phase synthesis method or a liquid-phase synthesis method; for example, when the peptide is synthesized by a solid-phase synthesis method, a solid-phase carrier to which the peptide was bound is treated with hydrogen fluoride thereby releasing the peptide from the solid-phase carrier and simultaneously removing a protective group from its amino acid side chain, whereby the objective peptide can be obtained. The crude peptide product thus obtained can be isolated and purified for example by solvent extraction, distillation, column chromatography, liquid chromatography, recrystallization etc.

When the antigen is prepared by using a transformant containing a DNA encoding the antigen, a DNA probe or primers designed on the basis of the amino acid sequence of the antigen, for example, are used to give a transformant containing a DNA encoding the antigen. By culturing this transformant in a usual manner, the objective peptide is produced intracellularly or extracellularly. The produced peptide can be purified by usual purification methods such as ultrafiltration, molecular-sieve chromatography, adsorption chromatography and high performance liquid chromatography.

Now, the method for producing the monoclonal antibody of the present invention by using the peptide antigen obtained in the manner described above is described in detail.

First, an animal is immunized with the above antigen. The antigen may be insolubilized and used directly in immunization or may be conjugated with a carrier protein prior to immunization. The carrier protein includes, but is not limited to, various proteins known in the art, such as ovalbumin, γ-globulin, keyhole limpet hemocyanin (KHL), BSA, etc. The method of conjugating the antigen with the carrier protein can include a method of using an SH group of a cysteine residue (MBS method), a method of using an amino group (bisimide ester method, glutaraldehyde method), a method of using phenol (bis-diazobentidine method), and a method of using a carboxyl group (carbodiimide method). In these methods, various crosslinking agents can be used; for example, glutaraldehyde, m-maleimide benzoyl-N-hydroxysuccinimide ester, carbodiimide, bis-bisazobenzidine, etc. can be used. The animal can include a rabbit, mouse, rat, goat, sheep, hamster, chicken etc. The immunization is carried out by administering the antigen or its conjugate, for example intraperitoneally, intravenously or subcutaneously, into the animal, wherein a suitable adjuvant such as complete Freund's adjuvant, incomplete Freund's adjuvant, an aluminum hydroxide adjuvant or the like may be administered together with the antigen. Administration of the antigen is carried out usually once at 1- to 6-week intervals and 2 to 10 times in total. In measurement of antibody titer in serum, it is possible to use any methods known in the art, such as radioimmunoassay (RIA), enzyme immunoassay (EIA), enzyme-linked immunosorbent assay (ELISA) and fluorescence immunoassay (FIA), among which ELISA is preferable from the viewpoint of detection sensitivity, rapidity, etc. The monoclonal antibody of the present invention is prepared from the animal showing a sufficient antibody titer against the antigen used in immunization.

The spleen or lymph node is excised from the animal showing a sufficient antibody titer, and antibody-producing cells (spleenocytes or lymphocytes) contained therein are fused with myeloma cells, thereby preparing monoclonal antibody-producing hybridomas.

The antibody-producing cells can be collected by any methods known in the art; for example, in the case of spleenocytes, the spleen is excised from the animal by cutting both sides of the spleen, and then pushed out and filtered with a gauze thereby giving spleenocytes to be used in fusion.

Myeloma cells used in cell fusion are not particularly limited and can be selected suitably from known cell strains. The myeloma cells can include P3-X63Ag8-U1 (P3U1), NS-1, SP2/0, X63.653, P3-X63Ag8 (P3), and FO, among which P3U1 is particularly preferable. These cell strains are subcultured in a suitable medium, for example, 8-azaguanine medium (a medium prepared by adding 8-azaguanine to a normal medium that is PRMI-1640 medium supplemented with glutamine, 2-mercaptoethanol, gentamicin and fetal bovine serum), and after the medium is exchanged with a normal medium 3 to 4 days before cell fusion, the cells are subcultured so that the cells, preferably at least $2 \times 10^7$ cells, are secured on the day of cell fusion.

Fusion of the immunized antibody-producing cells with the myeloma cells and subsequent selection of hybridomas can be carried out by methods known in the art. The method of cell fusion can include, for example, a method of using Sendai virus, a chemical method of using a high-molecular-weight polymer such as polyethylene glycol, and electroporation with high-voltage pulsing. For example, in the method of using polyethyleneglycol, the ratio of the antibody-producing cells to the myeloma cells is preferably in the range of from about 1 to 10 (the antibody-producing cells:the myeloma cells=about 1:1 to 10:1), and these cells can be fused by incubation in the presence of polyethylene glycol with a molecular weight of 1000 to 6000 added at a concentration of 10 to 50%, usually at room temperature, preferably 37° C., usually for 5 minutes. Selection of the hybridoma can be carried out usually by culturing the unfused cells and hybridomas in a HAT medium (medium prepared by adding hypoxanthine, aminopterin and thymidine to the normal medium), and then selectively proliferating only the hybridomas that have attained aminopterin resistance.

In cloning of the hybridomas thus obtained, it is possible to use methods known in the art, including for example a methyl cellulose method, a soft agarose method, a limiting dilution method etc., among which the limiting dilution method is preferable. In this method, the hybridomas are cultured for example in a medium usually for about 1 to 2 weeks, and those hybridomas recognized to show an antibody titer against the immunogen are screened additionally twice or so by the limiting dilution method, and the hybridoma recognized to stably show a high antibody titer is selected as a hybridoma strain producing the monoclonal antibody of the present invention. Measurement of the antibody titer can be carried out in accordance with the above-described method of measuring an antibody titer in antiserum.

The hybridoma strains thus cloned include hybridoma P53No. 18 4B (Accession No. FERM ABP-10561, internationally deposited on Feb. 18, 2005), hybridoma P53No. 17 16B (Accession No. FERM AP-20478, deposited on Mar. 25, 2005), hybridoma P53No. 23 1C (Accession No. FERM AP-20479, deposited on Mar. 25, 2005), hybridoma P53No. 5 16A (Accession No. FERM ABP-10562, internationally deposited on Mar. 25, 2005), hybridoma P53No. 10 6A (Accession No. FERM ABP-10563, internationally deposited on Mar. 25, 2005), and hybridoma P53No. 2 20G (Accession No. FERM AP-20480, deposited on Mar. 29, 2005), and these hybridomas have been deposited with International Patent Organism Depositary (IPOD), National Institute of Advanced Industrial Science and Technology (AIST), Japan.

Preferable among the above hybridoma strains are hybridoma P53No. 18 4B (Accession No. FERM ABP-10561), hybridoma P53No. 5 16A (Accession No. FERM ABP-10562) and hybridoma P53No. 10 6A (Accession No. FERM ABP-10563).

Other hybridoma strains cloned as described above include P53No. 3 3Bc (Accession No. FERM ABP-10576), P53No. 4 13C (Accession No. FERM ABP-10577), P53No. 11 7C (Accession No. FERM ABP-10578), P53No. 12 1A (Accession No. FERM ABP-10579), P53No. 22 11B (Accession No. FERM ABP-10580) and P53No. 23 1A (Accession No. FERM ABP-10581), and these hybridoma strains have been deposited since Mar. 27, 2006 with International Patent Organism Depositary (IPOD), National Institute of Advanced Industrial Science and Technology (AIST), Japan.

The hybridoma obtained in the manner described above is cultured in a suitable medium, and its culture supernatant is purified by methods known in the art, whereby the monoclonal antibody of the present invention can be produced. This method can be preferably used in obtaining the monoclonal antibody with high purity. In addition, the hybridoma, when injected intraperitoneally into a mouse, becomes an ascites cancer to give an ascites containing the monoclonal antibody of the present invention. By purifying this ascites by methods known in the art, the monoclonal antibody of the present invention can also be produced. This method can be used preferably in producing the monoclonal antibody in a large amount. The known methods of purifying the monoclonal antibody can include, for example, ammonium sulfate precipitation, gel filtration, ion-exchange chromatography, affinity chromatography etc.

Using the monoclonal antibody of the present invention obtained in the manner described above, the modification state after translation of p53 protein can be detected and quantified in a manner specific to a modification site. In specific detection and measurement, any methods known in the art, such as radioimmunoassay (RIA), enzyme immunoassay (EIA), enzyme-linked immunosorbent assay (ELISA), fluorescence immunoassay (FIA) and luminescence immunoassay, can be used. These measurement methods can be carried out according to techniques of general competition methods and sandwich methods.

According to the present invention, there is provided an antibody microarray comprising the monoclonal antibody of the invention immobilized on a substrate. As used herein, the antibody microarray (also called an antibody chip or a protein chip) refers to a device having antibodies arrayed and immobilized on a substrate.

The antibody microarray of the present invention may contain one or more kinds of the monoclonal antibody described above, and the number of the monoclonal antibodies immobilized on a substrate is not particularly limited. The monoclonal antibody immobilized on a substrate includes antibody fragments such as Fv, Fab, F (ab')$_2$, scFv and dsFv, and its biological species or production method is not particularly limited. The antibody microarrays also include antibody microarrays without using hybridomas, that is, those produced using antibodies such as hybrid antibodies, modified antibodies, chimeric antibodies and humanized antibodies. An antibody microarray having plural types of the monoclonal antibody immobilized thereon can simultaneously and comprehensively detect the presence and degrees of modification after translation of p53 in one sample in a manner specific to modification sites and can be used preferably in profiling of p53 modified after translation and in detection of a modification after translation signal pathway.

The monoclonal antibody to be immobilized on the substrate can be labeled arbitrarily with a suitable labeling substance, depending on its intended use. The labeling substance is selected suitably depending on the intended use; for example, it is possible to use enzymes such as horseradish peroxidase, β-D-galactosidase, alkali phosphatase, glucose-6-dehydrogenase and acetylcholine esterase, and fluorescent substances such as Cy3, Cy5 and fluorescein isothiocyanate (FITC), as well as radioisotopes, biotin etc. Instead of labeling the antigen of the present invention, a secondary antibody or protein A which specifically binds to the antibody of the present invention may be labeled and used.

The antibody microarray described above can be prepared by immobilizing the monoclonal antibody on a substrate. The material, size and shape of the substrate are not particularly limited. As the substrate for the antibody microarray, it is possible to use any substrates known in the art, for example substrates made of glass, polystyrene, nitrocellulose, and vinylidene fluoride, and such substrates may be subjected to chemical surface treatment (treatment with silane, amine, aldehyde, thiol, epoxy, or active ester) or may be coated with gold, aluminum, a cationic polymer such as polylysine, or a hydrophilic polymer such as polyacrylamide gel and agarose gel. Specifically, the substrates can be exemplified by those of high-density amino group introduction type, aminosilane coat type, poly-L-lysine type, aldehyde group introduction type, and commercial coated slide glass such as Takara-Hubble Slide Glass, and a coat for microarray for immobilization of X group-amino modified oligodeoxynucleotide is preferable in that signals can be stably obtained.

As a method of immobilizing the antibody on the substrate, it is possible to use any methods known in the art, such as optical lithography, microstamping, mechanical microspotting (contact type), micropipetting, microdispensing (non-contact type), jet printing, electrospray deposition (ESD), nanolithography, etc. The antibody thus micro-arrayed on the substrate is then immobilized via physical adsorption, ion bonding, covalent bonding (amide linkage, Schiff base, ether linkage, disulfide linkage, chemical crosslink, photoimmobilization etc.) and affinity bonding (GST tag, His tag, biotin-avidin) depending on the type of the substrate, among which the covalent bonding is preferable for stabilization and higher sensitization. When coating slide glass is used as the substrate, the coating slide glass may be pretreated as necessary. A spotting solution used in spotting of the antibody can be a spotting solution known in the art, and is preferably an isotonic solution, more preferably PBS. Spotting can be carried out by using an arraying machine known in the art. After spotting, blocking treatment is preferably conducted as necessary in order to prevent nonspecific reaction. The blocking solution used may be suitably selected from blocking solutions known in the art, and is preferably ethanolamine, glycine or BSA, more preferably ethanolamine.

The detection and measurement methods of using the antibody microarray of the present invention include a method detecting the signal intensity of a fluorescent dye, a detection method of utilizing enzymatic chemoluminescence, a method of utilizing a surface plasmon resonance phenomenon, a method of utilizing a mass spectrum and a method for electrochemical measurement. The method of detecting the signal intensity of a fluorescent dye can include, for example, a method wherein a protein in a sample is labeled with Cy5 and a control protein is labeled with Cy3, and these proteins are mixed and then contacted with the antibody microarray of the present invention, and a difference in fluorescence color between the proteins is utilized. Alternatively, the protein in a sample may be labeled with biotin and detected by the antibody microarray of the present invention. The method of utilizing enzyme chemoluminescence, for example in the case of sandwich method involves binding an antigen to the antibody microarray of the present invention and then binding a biotin-labeled secondary antibody thereto, whereby its chemoluminescence can be detected with streptavidin-labeled horseradish peroxidase. In the case of electrochemical method, an electroconductive substance is used as a base material on which the monoclonal antibody is immobilized as a probe, and the base material can be used as an electrode.

According to the antibody microarray of the present invention, modified states in a plurality of modification sites after translation on p53 can be detected simultaneously and comprehensively. For example, p53 protein derived from a cell undergoing stress is reacted with the antibody microarray of the present invention. As a result, if it is found that for example, a lysine residue at position 373 has been acetylated and a serine residue at position 392 has been phosphorylated, it is possible to reveal the modified states of the modification sites in p53 in the cell having undergone this stress.

In another aspect, the antibody microarray of the present invention can be used in diagnosis of diseases (particularly cancers). For example, p53 protein derived from a certain cancer patient is labeled with Cy5, while p53 protein derived from a healthy subject is labeled with Cy3, and then these proteins are mixed, then contacted with the antibody microarray of the present invention and measured for the fluorescence intensity of a fluorescent dye with a microarray reader using a commercial laser, whereby the state of modification after translation of p53 derived from the cancer patient can be detected and quantified. In another aspect, the antibody microarray of the present invention can be used in screening for compounds useful as anticancer agents or immunosuppressive agents.

According to the present invention, there is also provided a kit for measuring modification after translation of p53 protein, which comprises the monoclonal antibody of the present invention and/or the antibody microarray of the present invention. According to the measurement kit of the present invention, the state of modification after translation of p53 protein can be measured easily and rapidly. The monoclonal antibody contained in the measurement kit of the present invention, and the antibody probe immobilized on the antibody array, are preferably labeled with suitable labeling substances for facilitating detection and are particularly preferably labeled with FITC or biotin.

The measurement kit of the present invention can contain not only the monoclonal antibody or antibody microarray of the present invention but also arbitrary other reagents required for carrying out measurement and detection. Specifically, such reagents can be exemplified by the modified peptide antigen or fluorescently labeled modified peptide antigen, the assay buffer, the antibody for detection, the fluorescently labeled secondary antibody, the blocking solution, etc., and further by the substrate, the coloring agent etc. where an enzyme label is used.

According to the present invention, there can also be provided with a method for measuring a modification state after translation of p53 protein, which comprises using the monoclonal antibody or antibody microarray of the present invention. According to this method, a modification state after translation of p53 protein can be measured easily and rapidly.

The measurement method can be carried out for example as follows: Cells are cultured under conditions for loading the cells with various stresses, and then p53 is prepared therefrom. Then, the prepared p53 is contacted (reacted) with the monoclonal antibody of the present invention, and the state of modification after translation of p53 under the stress conditions is site-specifically detected. The antibody microarray of the present invention can be preferably used to measure modified states in a plurality of modification sites after translation on p53 simultaneously and comprehensively.

As another embodiment, a method of diagnosing a cancer which comprises using the monoclonal antibody or antibody microarray of the present invention can also be provided according to the present invention. Specifically, p53 protein derived from a certain cancer patient for example is labeled with Cy5, while p53 protein derived from a healthy subject is labeled with Cy3, and then these proteins are mixed and contacted with the monoclonal antibody or antibody microarray of the present invention to measure a difference in dye fluorescence intensity there between, whereby the state of modification after translation of p53 derived from the cancer patient can be detected, quantified, and utilized in diagnosis of the cancer. There can also be provided a method of screening for a compound useful as an anticancer agent, which comprises using the monoclonal antibody or antibody microarray of the present invention. According to the present invention, there can further be provided a pharmaceutical composition and an anticancer agent, which comprise the monoclonal antibody of the present invention as an active ingredient.

EXAMPLES

Hereinafter, the present invention is described in more detail by reference to the examples illustrating the constitution and effect of the invention. However, the present invention is not limited to these examples.

Example 1

(1) Selection and Synthesis of Antigen Peptide

In the p53 protein consisting of 393 amino acid residues, peptide sequences each containing an objective modification site after translation of p53 were designed and synthesized. These peptides had cysteine added to the N- or C-terminal thereof, the N-terminal α-amino group of which was protected with an acetyl group. As shown in table 1 (in the table, Ac represents an acetyl group, S(P) represents phosphorylated serine, T(P) represents phosphorylated threonine, and K(Ac) represents acetylated lysine), the synthesized peptides are as follows: modified peptides consisting of amino acid sequences represented by SEQ ID NOS: 25 to 47 respectively, unmodified peptides consisting of amino acid sequences represented by SEQ ID NOS: 48 to 70 respectively (that is, peptides having the amino acid sequences represented by SEQ ID NOS: 25 to 47 respectively and being not phosphorylated or acetylated), and modified peptides consisting of amino acid sequences represented by SEQ ID NOS: 71 to 93 respectively (that is, modified peptides having the amino acid sequences represented by SEQ ID NOS: 25 to 47 respectively and having one or two amino acid residues added to the N-terminal thereof). The synthesis method is described below.

TABLE 1

Synthesized antigen peptides

| SEQ ID NO: | Sequence Name | Amino Acid Sequence |
|---|---|---|
| 25 | Ac-1-12(6P)-C | Ac-MEEPQ-S(P)-DPSVEP-C |
| 26 | Ac-4-15(9P)-C | Ac-PQSDP-S(P)-VEPPLS-C |
| 27 | Ac-11-22(15P)-C | Ac-EPPL-S(P)-QETFSDL-C |
| 28 | Ac-13-24(18P)-C | Ac-PLSQE-T(P)-FSDLWK-C |
| 29 | AC-15-26(20P)-C | Ac-SQETF-S(P)-DLWKLL-C |
| 30 | Ac-27-39(33P)-C | Ac-PENNVL-S(P)-PLPSQA-C |

TABLE 1-continued

Synthesized antigen peptides

| SEQ ID NO: | Sequence Name | Amino Acid Sequence |
|---|---|---|
| 31 | Ac-32-43(37P)-C | Ac-LSPLP-S(P)-QAMDDL-C |
| 32 | Ac-41-52(46P)-C | Ac-DDLML-S(P)-PDDIEQ-C |
| 33 | Ac-50-61(55P)-C | Ac-IEQWF-T(P)-EDPGPD-C |
| 34 | Ac-76-87(81P)-C | Ac-APAAP-T(P)-PAAPAP-C |
| 35 | Ac-85-96(90P)-C | Ac-PAPAP-S(P)-WPLSSS-C |
| 36 | Ac-310-321(315P)-C | Ac-NNTSS-S(P)-PQPKKK-C |
| 37 | Ac-366-377(371P)-C | Ac-SSHLK-S(P)-KKGQST-C |
| 38 | Ac-371-382(376P)-C | Ac-SKKGQ-S(P)-TSRHKK-C |
| 39 | Ac-C-372-385(378P) | Ac-C-KKGQST-S(P)-RHKKLMF |
| 40 | Ac-C-385-393(392P) | Ac-C-FKTEGPD-S(P)-D |
| 41 | Ac-300-311(305Ac)-C | Ac-PPGST-K(Ac)-RALPNN-C |
| 42 | Ac-315-325(320Ac)-C | Ac-SPQPK-K(Ac)-KPLDG-C |
| 43 | Ac-365-375(370Ac)-C | Ac-HSSHL-K(Ac)-SKKGQ-C |
| 44 | Ac-367-377(372Ac)-C | Ac-SHLKS-K(Ac)-KGQST-C |
| 45 | Ac-368-378(373Ac)-C | Ac-HLKSK-K(Ac)-GQSTS-C |
| 46 | Ac-376-386(381Ac)-C | Ac-STSRH-K(Ac)-KLMFK-C |
| 47 | Ac-377-387(382Ac)-C | Ac-TSRHK-K(Ac)-LMFKT-C |
| 48 | Ac-1-12-C | Ac-MEEPQSDPSVEP-C |
| 49 | Ac-4-15-C | Ac-PQSDPSVEPPLS-C |
| 50 | Ac-11-22-C | Ac-EPPLSQETFSDL-C |
| 51 | Ac-13-24-C | Ac-PLSQETFSDLWK-C |
| 52 | Ac-15-26-C | Ac-SQETFSDLWKLL-C |
| 53 | Ac-27-39-C | Ac-PENNVLSPLPSQA-C |
| 54 | Ac-32-43-C | Ac-LSPLPSQAMDDL-C |
| 55 | Ac-41-52-C | Ac-DDLMLSPDDIEQ-C |
| 56 | Ac-50-61-C | Ac-IEQWFTEDPGPD-C |
| 57 | Ac-76-87-C | Ac-APAAPTPAAPAP-C |
| 58 | Ac-85-96-C | Ac-PAPAPSWPLSSS-C |
| 59 | Ac-310-321-C | Ac-NNTSSSPQPKKK-C |
| 60 | Ac-366-377-C | Ac-SSHLKSKKGQST-C |
| 61 | Ac-371-382-C | Ac-SKKGQSTSRHKK-C |
| 62 | Ac-C-372-385 | Ac-C-KKGQSTSRHKKLMF |
| 63 | Ac-C-385-393 | Ac-C-FKTEGPDSD |
| 64 | Ac-300-311-C | Ac-PPGSTKRALPNN-C |
| 65 | Ac-315-325-C | Ac-SPQPKKKPLDG-C |
| 66 | A6-365-375-C | Ac-HSSHLKSKKGQ-C |
| 67 | Ac-367-377-C | Ac-SHLKSKKGQST-C |
| 68 | Ac-368-378-C | Ac-HLKSKKGQSTS-C |
| 69 | Ac-376-386-C | Ac-STSRHKKLMFK-C |
| 70 | Ac-377-387-C | Ac-TSRHKKLMFKT-C |
| 71 | 1-12(6P)-C | MEEPQ-S(P)-DPSVEP-C |
| 72 | 3-15(9P)-C | EPQSDP-S(P)-VEPPLS-C |
| 73 | 10-22(15P)-C | VEPPL-S(P)-QETFSDL-C |
| 74 | 12-24(18P)-C | PPLSQE-T(P)-FSDLWK-C |
| 75 | 14-26(20P)-C | LSQETF-S(P)-DLWKLL-C |
| 76 | 26-39(33P)-C | LPENNVL-S(P)-PLPSQA-C |
| 77 | 31-43(37P)-C | VLSPLP-S(P)-QAMDDL-C |
| 78 | 40-52(46P)-C | MDDLML-S(P)-PDDIEQ-C |
| 79 | 49-61(55P)-C | DIEQWF-T(P)-EDPGPD-C |
| 80 | 75-87(81P)-C | PAPAAP-T(P)-PAAPAP-C |
| 81 | 84-96(90P)-C | APAPAP-S(P)-WPLSSS-C |
| 82 | 309-321(315P)-C | PNNTSS-S(P)-PQPKKK-C |
| 83 | 365-377(371P)-C | HSSHLK-S(P)-KKGQST-C |
| 84 | 370-382(376P)-C | KSKKGQ-S(P)-TSRHKK-C |
| 85 | 371-385(378P) | SKKGQST-S(P)-RHKKLMF |
| 86 | 384-393(392P) | MFKTEGPD-S(P)-D |
| 87 | 299-311(305Ac)-C | LPPGST-K(Ac)-RALPNN-C |
| 88 | 314-325(320Ac)-C | SSPQPK-K(Ac)-KPLDG-C |
| 89 | 364-375(370Ac)-C | AHSSHL-K(Ac)-SKKGQ-C |
| 90 | 366-377(372Ac)-C | SSHLKS-K(Ac)-KGQST-C |
| 91 | 367-378(373Ac)-C | SHLKSK-K(Ac)-GQSTS-C |
| 92 | 375-386(381Ac)-C | QSTSRH-K(Ac)-KLMFK-C |
| 93 | 376-387(382Ac)-C | STSRHK-K(Ac)-LMFKT-C |

Peptide synthesis was carried out by a manual solid-phase synthesis method using Fmoc chemistry. The synthesis scale was 0.2 mmol, and phosphorylated serine ($Ser^{(P)}$), phosphorylated threonine ($Thr^{(P)}$), and acetylated lysine ($Lys^{(Ac)}$) were introduced by using Fmoc-Ser (PO(OBzl)OH)—OH, Fmoc-Thr(PO(OBzl)-OH)—OH, and Fmoc-Lys(Ac)—OH, respectively (table 2: Fmoc-amino acid residues). The N-terminal thereof was acetylated with acetic anhydride (1 mmol). Each synthesized peptide was released from the resin and subjected to de-protection reaction with Reagent K (82.5% trifluoroacetic acid, 5% water, 5% thioanisole, 5% phenol, 2.5% 1,2-ethanedithiol) at room temperature for 3 hours.

TABLE 2

Fmoc-amino acid residues

| | Fmoc-AA-OH | MW |
|---|---|---|
| A | Fmoc-Ala-OH | 311.3 |
| R | Fmoc-Arg(Pmc)-OH | 662.8 |
| C | Fmoc-Cys(Trt)-OH | 585.7 |
| Q | Fmoc-Gln(Trt)-OH | 610.7 |
| E | Fmoc-Glu(otBu)-OH | 425.5 |
| G | Fmoc-Gly-OH | 297.3 |
| H | Fmoc-His(Trt)-OH | 619.7 |
| I | Fmoc-Ile-OH | 353.4 |
| L | Fmoc-Leu-OH | 353.4 |
| K | Fmoc-Lys(Boc)-OH | 468.5 |
| M | Fmoc-Met-OH | 371.5 |
| F | Fmoc-Phe-OH | 387.4 |
| P | Fmoc-Pro-OH | 337.4 |
| Ser(P) | Fmoc-Ser(PO(Obzl)OH)-OH | 497.44 |
| S | Fmoc-Ser(tBu)-OH | 383.4 |
| Thr(P) | Fmoc-Thr(PO(Obzl)OH)-OH | 511.5 |
| T | Fmoc-Thr(tBu)-OH | 397.5 |
| w | Fmoc-Trp-OH | 426.5 |
| Y | Fmoc-Tyr(tBu)-OH | 459.6 |
| V | Fmoc-Val-OH | 339.4 |
| N | Fmoc-Asn(Trt)-OH | 596.7 |
| D | Fmoc-Asp(otBu)-OH | 411.5 |
| Lys(Ac) | Fmoc-Lys(Ac)-OH | 410.5 |

The peptide obtained as described above was purified by reverse phase liquid chromatography on PRE-PACKED COLUMN RT 250-20 (MIGHTYSIS RP-18 GP 5 µm). The peptide was eluted with 0.05% TFA-acetonitrile linear density gradient. Fractions containing the purified peptide were recovered and lyophilized. The purity of the finally purified peptide was confirmed by high performance liquid chromatography on analytical PRE-PACKED COLUMN RT 250-4.6 (MYGHTYSIS RP-18 GP 5 µm) and with MALDI-TOF mass analysis apparatus (Voyager DE-PRO, manufactured by Applied Biosystems). The results of mass analysis of each of the peptides thus obtained are shown in table 3.

TABLE 3

Results of mass analysis of the synthesized peptides

| No. | Sequence Name | MW | Measurement Value |
|---|---|---|---|
| 25 | Ac-1-12(6P)-C | | |
| 26 | Ac-4-15(9P)-C | 1477.53 | 1503.76 |
| 27 | Ac-11-22(15P)-C | 1587.62 | 1586.97 |
| 28 | Ac-13-24(18P)-C | 11675.8 | 1677.75 |
| 29 | Ac-15-26(20P)-C | | |
| 30 | Ac-27-39(33P)-C | | |
| 31 | Ac-32-43(37P)-C | 1511.65 | 1511.63 |
| 32 | Ac-41-52(46P)-C | 1615.66 | 1615.11 |
| 33 | Ac-50-61(55P)-C | 1658.65 | 1658.93 |
| 34 | Ac-76-87(81P)-C | 1256.37 | 1256.54 |
| 35 | Ac-85-96(90P)-C | 1421.52 | 1421.61 |
| 36 | Ac-310-321(315P)-C | 1540.61 | 1543.92 |
| 37 | Ac-366-377(371P)-C | 1512.72 | 1513.49 |
| 38 | Ac-371-382(376P)-C | 1596.72 | 1597.89 |
| 39 | Ac-C-372-385(378P) | | |
| 40 | Ac-C-385-393(392P) | 1220.17 | 1220.27 |
| 41 | Ac-300-311(305Ac)-C | 1438.58 | 1439.63 |
| 42 | Ac-315-325(320Ac)-C | | |
| 43 | Ac-365-375(370Ac)-C | 1423.56 | 1424.7 |
| 44 | Ac-367-377(372Ac)-C | 1387.52 | 1388.03 |
| 45 | Ac-368-378(373Ac)-C | | |
| 46 | Ac-376-386(381Ac)-C | 1549.81 | 1551.57 |
| 47 | Ac-377-387(382Ac)-C | | |
| 48 | Ac-1-12-C | | |

TABLE 3-continued

Results of mass analysis of the synthesized peptides

| No. | Sequence Name | MW | Measurement Value |
|---|---|---|---|
| 49 | Ac-4-15-C | | |
| 50 | Ac-11-22-C | 1507.62 | 1530.11 |
| 51 | Ac-13-24-C | 1595.77 | 1597.03 |
| 52 | Ac-15-26-C | | |
| 53 | Ac-27-39-C | | |
| 54 | Ac-32-43-C | | |
| 55 | Ac-41-52-C | 1535.66 | 1535.87 |
| 56 | Ac-50-61-C | 1578.65 | 1578.99 |
| 57 | Ac-76-87-C | 1176.37 | 1175.47 |
| 58 | Ac-85-96-C | 1341.52 | 1341.77 |
| 59 | Ac-310-321-C | | |
| 60 | Ac-366-377-C | 1432.6 | 1433.08 |
| 61 | Ac-371-382-C | 1516.72 | 1517.46 |
| 62 | Ac-C-372-385 | | |
| 63 | Ac-C-385-393 | | |
| 64 | Ac-300-311-C | 1396.58 | 1396.97 |
| 65 | Ac-315-325-C | 1339.52 | 1340.79 |
| 66 | Ac-365-375-C | 1381.56 | 1382.73 |
| 67 | Ac-367-377-C | 1345.52 | 1346.43 |
| 68 | Ac-368-378-C | 1345.52 | 1346.64 |
| 69 | Ac-376-386-C | 1507.81 | 1508.39 |
| 70 | Ac-377-387-C | | |
| 71 | 1-12(6P)-C | 1527.53 | 1527.02 |
| 72 | 3-15(9P)-C | 1564.59 | 1565.32 |
| 73 | 10-22(15P)-C | 1643.7 | 1645.79 |
| 74 | 12-24(18P)-C | 1730.84 | 1732.94 |
| 75 | 14-26(2OP)-C | 1761.92 | 1763.83 |
| 76 | 26-39(33P)-C | 1661.79 | 1663.75 |
| 77 | 31-43(37P)-C | 1568.72 | 1604.54 |
| 78 | 40-52(46P)-C | 1704.8 | 1704.75 |
| 79 | 49-61(55P)-C | 1731.69 | 1732.09 |
| 80 | 75-87(81P)-C | 1311.44 | 1311.51 |
| 81 | 84-96(90P)-C | 1450.55 | 1450.83 |
| 82 | 309-321(315P)-C | 1595.65 | 1594.87 |
| 83 | 365-377(371P)-C | 1607.69 | 1609.12 |
| 84 | 370-382(376P)-C | 1682.84 | 1683.89 |
| 85 | 371-385(378P) | 1843.06 | 1841.26 |
| 86 | 384-393(392P) | 1206.17 | 1205.15 |
| 87 | 299-311(305Ac)-C | 1509.69 | 1510.29 |
| 88 | 314-325(32OAc)-C | 1426.6 | 1427.77 |
| 89 | 364-375(370Ac)-C | 1452.59 | 1453.82 |
| 90 | 366-377(372Ac)-C | 1432.55 | 1433.5 |
| 91 | 367-378(373Ac)-C | 1431.55 | 1433.79 |
| 92 | 375-386(381Ac)-C | 1635.89 | 1636.59 |
| 93 | 376-387(382Ac)-C | 1607.86 | 1609.89 |

(2) Immunization of Animal and Preparation of Antibody-Producing Cell 1 mg/0.4 mL N-(m-maleimidobenzoyloxy)succinimide (referred to herein after as MBS (No. 22311 manufactured by PIERCE)) in N,N-dimethylformamide (herein after referred to as DMFA) was mixed with KLH (No. 77600, manufactured by PIERCE), and the mixture was reacted at room temperature for 1 hour and then subjected to a desalting column (Sephadex G-25, manufactured by Pharmacia) previously equilibrated with 0.05 M phosphate buffer, pH 7.4, thereby removing free MBS to give 10 mg KLH-maleimide. 10 mg KLH-maleimide was added to 5 mg of each of the modified peptides consisting of the amino acid sequences represented by SEQ ID NOS: 25 to 47 obtained in (1) above, and the mixture was reacted at room temperature for 2 hours, and each of the resulting peptide-KLH conjugates was used as an antigen.

The KLH conjugate, together with complete Freund's adjuvant (No. 5582, manufactured by ICN/Cappel), was administered subcutaneously in a dose of 50 µg conjugate/mouse at about 10 sites on the back of each of preliminarily bred BALB/c mice (5 mice were used for each of the peptides). Thereafter, each mouse was booster-immunized 5 times at 2-week intervals with the same amount of the immunogen together with complete Freund's adjuvant. Blood was collected through a tail vein of the mouse and measured for its serum antibody titer by the ELISA method in (3) below.

(3) ELISA Method for Measuring Antibody Titer

5 µg/ml of each of the antigen peptides synthesized in (1) above was pipetted in a volume of 100 µg/well onto a 96-well immuno-plate (manufactured by NUNC) and then left overnight at 4° C., thereby coating the plate with the antigen. Then, the solution was removed, then the plate was washed twice with a wash (PBS solution containing 0.2% Tween 20), and each well was filled with a wash and incubated at room temperature for 2 hours. After the solution was removed, 100 µl dilution of the antiserum (dilution obtained by 2-step dilution from a 1000-fold dilution of the antiserum) by diluted solution (PBS solution containing 0.05% Tween 20) was added to each well and incubated at room temperature for 2 hours. After incubation, the solution was removed, each well was washed 3 times with a wash, and then 100 µl horseradish peroxidase (HRPO)-bound goat anti-mouse IgG (manufactured by Biosource) was added to each well and incubated at room temperature for 2 hours. After incubation, the solution was removed, then each well was washed 3 times with a wash, a substrate solution (that is, a solution prepared by adding 5 µl hydrogen peroxide to a solution of 10 mg o-phenylene diamine in 25 ml citrate-phosphate buffer, pH 5.0) was added to the well in a volume of 100 µl/well and colored for 20 minutes, the coloration was terminated by adding 100 µl of 1M $H_2SO_4$, and each well was measured for absorbance at 492 nm with Immuno Reader (manufactured by BIO-RAD).

(4) Purification of Monoclonal Antibody

From the animal showing a sufficient antibody titer, the spleen was excised 4 days after the final immunization and then suspended in RPMI-1640 medium (manufactured by Invitrogen) to give a spleenocyte suspension. As myeloma cells used in cell fusion, BALB/c mouse-derived myeloma cells P3-X63-Ag8-U1 (3PU1) were used. The spleenocytes and myeloma cells were washed several times respectively in serum-free RPMI-1640 medium (manufactured by Invitrogen) containing 12.5 mM HEPES, then mixed with each other in a spleenocyte/myeloma cell ratio of 10/1, and centrifuged at room temperature to remove the medium. The precipitated cells were made well loose, and 1 ml polyethylene glycol (PEG, manufactured by Sigma) warmed at 37° C. was added thereto. The cells was well mixed with PEG and then left at 37° C. for about 5 minutes to effect cell fusion, then 15 ml TIL medium (manufactured by IBL) containing 10% fetal calf serum (FCS), warmed at 37° C., was added thereto dropwise over about 5 minutes, then 20 ml TIL medium containing 10% FCS was added thereto, and the cells were centrifuged at room temperature, followed by removing the supernatant under suction. Then, TIL medium containing 10% FCS, warmed at 37° C., was added to and mixed with the cells gently by pipetting, and 100 µl of the spleenocytes was pipetted in an amount of $2\times10^5$ spleenocytes/well onto a 96-well microplate. After 1 day, HAT medium (manufactured by Cosmo Bio Co., Ltd.) containing 10% FCS was added to the cells which were then cultured at 37° C. in 5% $CO_2$ gas. After 1 day, after 2 days and at 2- to 3-day intervals thereafter, half of the medium was removed under suction, and HAT medium containing 10% FCS was added instead. After 10 days to 2 weeks, half of the medium was removed under suction and exchanged with HT medium (manufactured by Gibco) containing 10% FCS, and at an appropriate time, the antibody-producing hybridoma was searched by the method of ELISA measurement in (5) below.

(5) Method of ELISA Measurement of Hybridoma Culture Supernatant

1 µg/ml of each of the antigen peptides synthesized in (1) above was pipetted in a volume of 50 µl/well onto a 96-well immuno-plate (manufactured by NUNC) and then left overnight at 4° C., thereby coating the plate with the antigen peptide. Then, the solution was removed, the plate was washed twice with a wash (PBS solution containing 0.2% Tween 20), and a PBS solution containing 1% BSA was added to each well and incubated at room temperature for 2 hours. After the solution was removed, 50 µl culture supernatant was added to each well and incubated at room temperature for 2 hours. After incubation, the solution was removed, each well was washed 3 times with a wash, and then 50 µl of a dilution obtained by diluting HRPO-bound goat anti-mouse IgG (manufactured by Biosource) 10.000-fold with a diluent (PBS solution containing 0.05% Tween 20) was added to each well and incubated at room temperature for 2 hours. After incubation, the solution was removed, each well was washed 3 times with a wash, a substrate solution (that is, a solution prepared by adding 5 µl hydrogen peroxide to a solution of 10 mg o-phenylene diamine in 25 ml citrate-phosphate buffer, pH 5.0) was added in a volume of 50 µl/well onto the plate and colored for 20 minutes, the coloration was terminated by adding 100 µl of 1M $H_2SO_4$, and each well was measured for absorbance at 492 nm with Immuno Reader (manufactured by BIO-RAD).

(6) Screening and Cloning of Antibody-Producing Hybridoma

The hybridomas obtained in the manner described above were screened for the hybridoma satisfying the following 3 conditions:

1. Positive to the immunization antigen modified peptide.
2. Positive to the peptide consisting of an antigen peptide having one amino acid residue added to the N-terminal thereof.
3. Negative to the peptide having the same sequence as that of the antigen peptide but being not modified (not phosphorylated or acetylated).

The method of ELISA measurement in (5) above was used in screening. Particularly for preparing the antibody reliably and efficiently, selected 20 wells were freeze-preserved after culture, and cloning of 5 wells+1 well was initiated, and when there was no suitable antibody in primary screening or in cloning, screening was conducted again with a sample starting from a one-stage earlier stock. For improving accuracy in ELISA measurement, screening of 3 types of peptides was conducted on the same plate.

Cloning was carried out by repeating the limiting dilution method and the ELISA measurement in (5) above several times, whereby the hybridoma of the present invention was obtained. The resulting hybridoma was visually judged as monoclonal.

The hybridoma strains thus cloned include hybridoma P53No. 18 4B (Accession No. FERM ABP-10561, internationally deposited on Feb. 18, 2005), hybridoma P53No. 17 16B (Accession No. FERM AP-20478, deposited on Mar. 25, 2005), hybridoma P53No. 23 1C (Accession No. FERM AP-20479, deposited on Mar. 25, 2005), hybridoma P53No. 5 16A (Accession No. FERM ABP-10562, internationally deposited on Mar. 25, 2005), hybridoma P53No. 10 6A (Accession No. FERM ABP-10563, internationally deposited on Mar. 25, 2005), and hybridoma P53No. 2 20G (Accession No. FERM AP-20480, deposited on Mar. 29, 2005), and these hybridomas have been deposited with International Patent Organism Depositary (IPOD), National Institute of Advanced Industrial Science and Technology (AIST), Japan.

Preferable among the above hybridoma strains are hybridoma P53No. 18 4B (Accession No. FERM ABP-10561), hybridoma P53No. 5 16A (Accession No. FERM ABP-10562) and hybridoma P53No. 10 6A (Accession No. FERM ABP-10563).

Other hybridoma strains cloned as described above include P53No. 3 3Bc (Accession No. FERM ABP-10576), P53No. 4 13C (Accession No. FERM ABP-10577), P53No. 11 7C (Accession No. FERM ABP-10578), P53No. 12 1A (Accession No. FERM ABP-10579), P53No. 22 11B (Accession No. FERM ABP-10580) and P53No. 23 1A (Accession No. FERM ABP-10581), and these hybridoma strains have been deposited since Mar. 27, 2006 with International Patent Organism Depositary (IPOD), National Institute of Advanced Industrial Science and Technology (AIST), Japan.

After cloning, the resulting hybridomas were cultured in a serum-free medium to yield the monoclonal antibodies of the present invention.

Using the method of ELISA measurement in (5) above, the reactivity of the monoclonal antibodies produced by the resulting hybridomas, with the modified antigen peptides and unmodified antigen peptides, was confirmed. Some of the results are shown in tables 4 and 5 (in the tables, "p53No. 17 16Ba", "p53No. 18 4Ba", etc. represent monoclonal antibodies produced by the respective cloned cells, and each numerical value is indicative of absorbance at 492 nm.)

TABLE 4

Reactivity of each monoclonal antibody with the modified antigen peptides and unmodified antigen peptides

| Monoclonal Antibody | AC-300-311(305Ac)-C | 299-311(305Ac)-C | Ac-300-311-C |
|---|---|---|---|
| p53No.17 16Aa | 2.663 | 2.795 | 0.21 |
| p53No.17 16Ba | 2.404 | 2.497 | 0.138 |
| p53No.17 16Da | 2.569 | 2.791 | 0.157 |
| p53No.17 16Ea | 2.315 | 2.508 | 0.125 |

| Monoclonal Antibody | Ac-315-325(320Ac)-C | 314-325(320Ac)-C | Ac-315-325-C |
|---|---|---|---|
| p53No.18 1Aa | 2.175 | 1.818 | 0.059 |
| p53No.18 1Ba | 2.294 | 1.981 | 0.059 |
| p53No.18 1Ca | 2.151 | 1.847 | 0.073 |
| p53No.18 1Da | 2.111 | 1.838 | 0.097 |
| p53No.18 4Aa | 2.647 | 2.38 | 0.117 |
| p53No.18 4Ba | 2.759 | 2.294 | 0.044 |
| p53No.18 4Ca | 2.637 | 2.303 | 0.081 |
| p53No.18 4Da | 2.655 | 2.262 | 0.092 |
| p53No.18 4Ea | 2.609 | 2.208 | 0.113 |
| p53No.18 4Fa | 2.312 | 2.209 | 0.126 |

| Monoclonal Antibody | Ac-377-387(382Ac)-C | 376-387(382Ac)-C | Ac-377-387-C |
|---|---|---|---|
| p53No.23 1Aa | 3.298 | 2.963 | 0.279 |
| p53No.23 1Ba | 2.093 | 2.149 | 0.061 |
| p53No.23 1Ca | 2.04 | 2.288 | 0.079 |
| p53No.23 1Da | 3.025 | 2.787 | 0.366 |

| Monoclonal Antibody | Ac-4-15(9P)-C | 3-15(9P)-C | Ac-4-15-C |
|---|---|---|---|
| p53No.2 20Ca | 0.95 | 0.866 | 0.09 |
| p53No.2 20Ga | 1.135 | 1.044 | 0.049 |
| p53No.2 20Ea | 1.179 | 1.08 | 0.055 |

| Monoclonal Antibody | Ac-15-26(20P)-C | 14-26(20P)-C | Ac-15-26-C |
|---|---|---|---|
| p53No.5 2Aa | 2.036 | 2.211 | 0.062 |
| p53No.5 2Ba | 2.054 | 2.177 | 0.057 |
| p53No.5 2Ca | 2.054 | 2.227 | 0.073 |
| p53No.5 2Da | 2.042 | 2.163 | 0.052 |
| p53No.5 9Aa | 2.753 | 2.65 | 0.167 |
| p53No.5 9Ba | 2.563 | 2.627 | 0.107 |
| p53No.5 9Ca | 2.738 | 2.672 | 0.095 |
| p53No.5 13Aa | 2.106 | 2.136 | 0.097 |
| p53No.5 13Ba | 2.17 | 2.205 | 0.087 |
| p53No.5 13Ca | 2.146 | 2.234 | 0.091 |
| p53No.5 13Da | 2.254 | 2.219 | 0.121 |
| p53No.5 16Aa | 2.245 | 2.286 | 0.053 |
| p53No.5 16Ba | 2.139 | 2.149 | 0.057 |
| p53No.5 16Ca | 2.657 | 2.693 | 0.053 |
| p53No.5 19Aa | 2.052 | 2.128 | 0.058 |
| p53No.5 19Ba | 2.011 | 2.164 | 0.058 |
| p53No.5 19Ca | 2.025 | 2.153 | 0.059 |

| Monoclonal Antibody | Ac-76-87(81P)-C | 75-87(81P)-C | Ac-76-87-C |
|---|---|---|---|
| p53No.10 2Aa | 3.076 | 2.772 | 0.042 |
| p53No.10 2Ba | 2.915 | 2.683 | 0.06 |
| p53No.10 2Ca | 2.573 | 2.379 | 0.042 |
| p53No.10 2Da | 2.728 | 2.114 | 0.053 |
| p53No.10 2Ea | 1.597 | 1.072 | 0.141 |
| p53No.10 2Fa | 2.445 | 2.226 | 0.04 |
| p53No.10 3Aa | 2.665 | 2.52 | 0.047 |
| p53No.10 6Aa | 3.5 | 3.487 | 0.075 |
| p53No.10 6Ba | 3.297 | 3.193 | 0.071 |
| p53No.10 6Ca | 3.26 | 3.214 | 0.88 |

As shown in table 4, it was confirmed that the monoclonal antibodies produced by the obtained hybridomas react specifically with the modified antigen peptides and the peptides consisting of a modified antigen peptide having one amino acid added to the N-terminal thereof, but do not react with the unmodified peptides.

TABLE 5

Reactivity of each monoclonal antibody with the modified antigen peptides and unmodified antigen peptides

| Monoclonal Antibody | Ac-11-22(15P)-C | 10-22(15P)-C | Ac-11-22-C |
|---|---|---|---|
| p53No.3 3Ba | 1.134 | 1.755 | 0.190 |
| p53No.3 3Bb | 2.016 | 2.299 | 0.546 |
| p53No.3 3Bc | 2.228 | 2.206 | 0.900 |

| Monoclonal Antibody | Ac-13-24(18P)-C | 12-24(18P)-C | Ac-13-24-C |
|---|---|---|---|
| p53No.4 13A | 1.876 | 2.347 | 0.153 |
| p53No.4 13B | 1.479 | 1.988 | 0.116 |
| p53No.4 13C | 1.832 | 2.258 | 0.211 |

| Monoclonal Antibody | Ac-50-61(55P)-C | 49-61(55P)-C | Ac-50-61-C |
|---|---|---|---|
| p53No.9 4A | 1.264 | 1.019 | 0.385 |

| Monoclonal Antibody | Ac-310-321(315P)-C | 309-321(315P)-C | Ac-310-321-C |
|---|---|---|---|
| p53No12 1A | 0.936 | 0.818 | −0.003 |
| p53No12 1B | 0.992 | 0.902 | −0.012 |
| p53No12 1C | 0.842 | 0.932 | −0.003 |
| p53No12 1D | 0.806 | 0.741 | −0.002 |
| p53No12 2A | 0.838 | 1.042 | −0.016 |
| p53No12 2B | 0.692 | 1.091 | −0.009 |
| p53No12 2C | 0.821 | 1.081 | 0.016 |
| p53No12 5B | 2.239 | 1.783 | 0.471 |
| p53No12 5E | 0.742 | 0.652 | 0.090 |
| p53No12 5G | 1.559 | 1.444 | 0.240 |

TABLE 5-continued

Reactivity of each monoclonal antibody with the modified antigen peptides and unmodified antigen peptides

| Monoclonal Antibody | Ac-85-96(90P)-C | 84-96(90P)-C | Ac-85-96-C |
|---|---|---|---|
| p53No.11 7A | 1.480 | 0.875 | 0.245 |
| p53No.11 7B | 1.799 | 1.131 | 0.292 |
| p53No.11 7C | 1.507 | 0.755 | 0.124 |

| Monoclonal Antibody | Ac-376-386(381Ac)-C | 375-386(381Ac)-C | Ac-376-386-C |
|---|---|---|---|
| p53No.22 11A | 0.452 | 0.333 | 0.078 |
| p53No.22 11B | 1.406 | 1.004 | 0.329 |
| p53No.22 11C | 0.516 | 0.313 | 0.104 |
| p53No.22 11D | 0.615 | 0.458 | 0.114 |

As shown in table 5, it was confirmed that the monoclonal antibodies produced by the obtained hybridomas react specifically with the modified antigen peptides and the peptides consisting of a modified antigen peptide having one amino acid added to the N-terminal thereof, but do not react with the unmodified peptides.

[Crossreactivity with the Phosphorylation-Recognizing Antibodies]

1 µl/ml peptide of each of SEQ ID NOS: 25 to 40 (phosphorylated modified antigen peptides) in Table 1 was pipetted in a volume of 50 µl/well onto a 96-well immuno-plate (manufactured by NUNC) and then left overnight at room temperature, thereby coating the plate with the antigen peptide. Then, the solution was removed, each well was washed 5 times with a wash (TBS solution containing 0.1% Tween 20), and 200 µl TBS solution containing 4% BSA was added to each well and incubated at room temperature for 2 hours. After incubation, the solution was removed, the plate was washed 5 times with a wash, and RPMI1640/10% FCS culture supernatant and COSMEDIUM culture supernatant (in the graph, (N) indicates COSMEDIUM culture supernatant) were added respectively in a volume of 45 µl to each well and incubated at room temperature for 2 hours. After incubation, the solution was removed, each well was washed 5 times with awash, and 40 µl dilution of HRP-bound goat anti-mouse IgG (Product No. Sc-2031, manufactured by Santa Cruz Biotechnology) prepared by diluting the IgG 5000-fold with a diluent (TBS solution containing 4% BSA and 0.1% Tween 20) was added to each well and incubated at room temperature for 30 minutes. After incubation, the solution was removed, each well was washed 5 times with a wash, and 100 µl substrate solution (o-phenylenediamine dihydrochloride (Sigma FAST) 50 set (Product No. P9187, manufactured by Sigma) was added to each well and reacted for 20 minutes. The coloration was terminated by adding 50 µl of 10% $H_2SO_4$, and each well was measured for absorbance at 490 nm with ImmunoMini NJ-2300 (manufactured by Nalge Nunc International). FIGS. 4 to 10 show the results of crossreactivity with the monoclonal antibodies. The absorbance at 490 nm is shown on the ordinate.

Figure 4:
FIG. 4 is a graph showing results of crossreactivity with a monoclonal antibody.

As shown in FIG. 4, it was confirmed that p53No. 3 3Ba, p53No. 3 3Bb, and p53No. 3 3Bc react specifically with phosphorylated modified Ser15. p53No. 3 3Ba(N) and p53No. 3 3Bb (N) were confirmed to react specifically with phosphorylated modified Ser15 even in the peptides allowed to react with COSMEDIUM culture supernatant.

Figure 5:
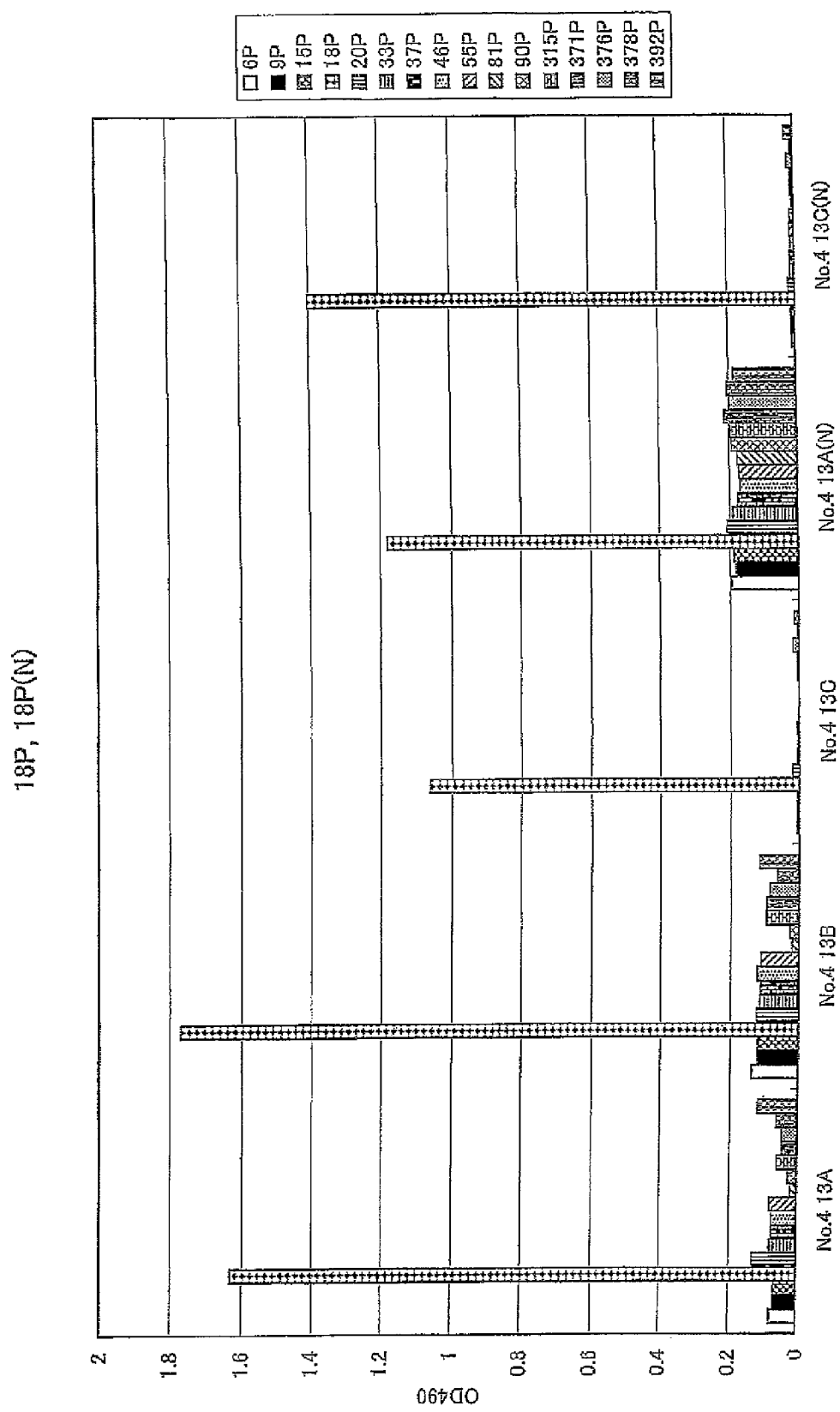
FIG. 5 is a graph showing results of crossreactivity with a monoclonal antibody.

As shown in FIG. 5, it was confirmed that p53No. 4 13A, p53No. 4 13B, and p53No. 4 13C react specifically with phosphorylated modified Thr18. p53No. 4 13A(N) and p53No. 4 13C(N) were confirmed to react specifically with phosphorylated modified Thr18 even in the peptides allowed to react with COSMEDIUM culture supernatant.

Figure 6:
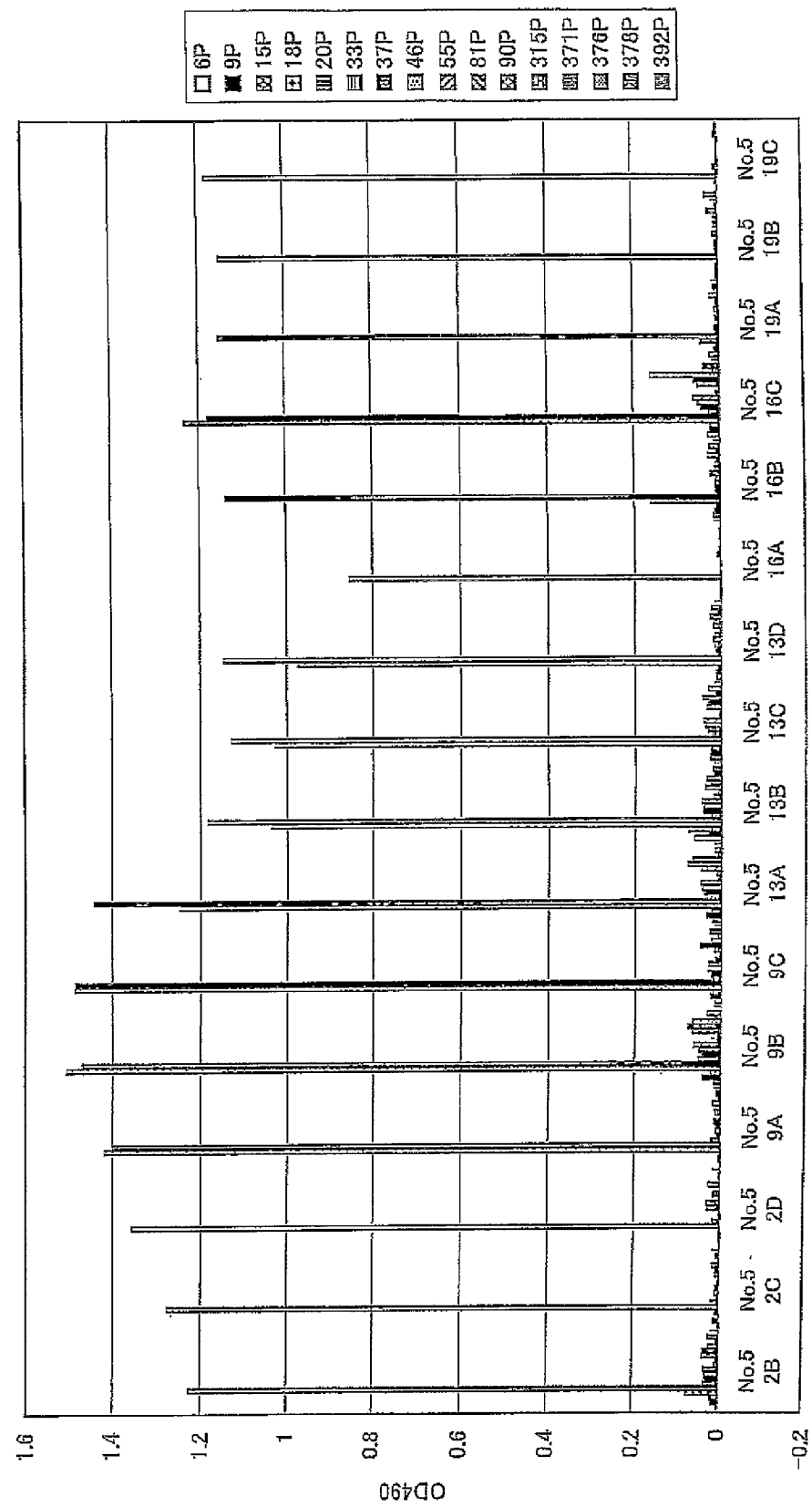
FIG. 6 is a graph showing results of crossreactivity with a monoclonal antibody.

As shown in FIG. 6, it was confirmed that p53No. 5 2B etc. react specifically with phosphorylated modified Ser20.

Figure 7:
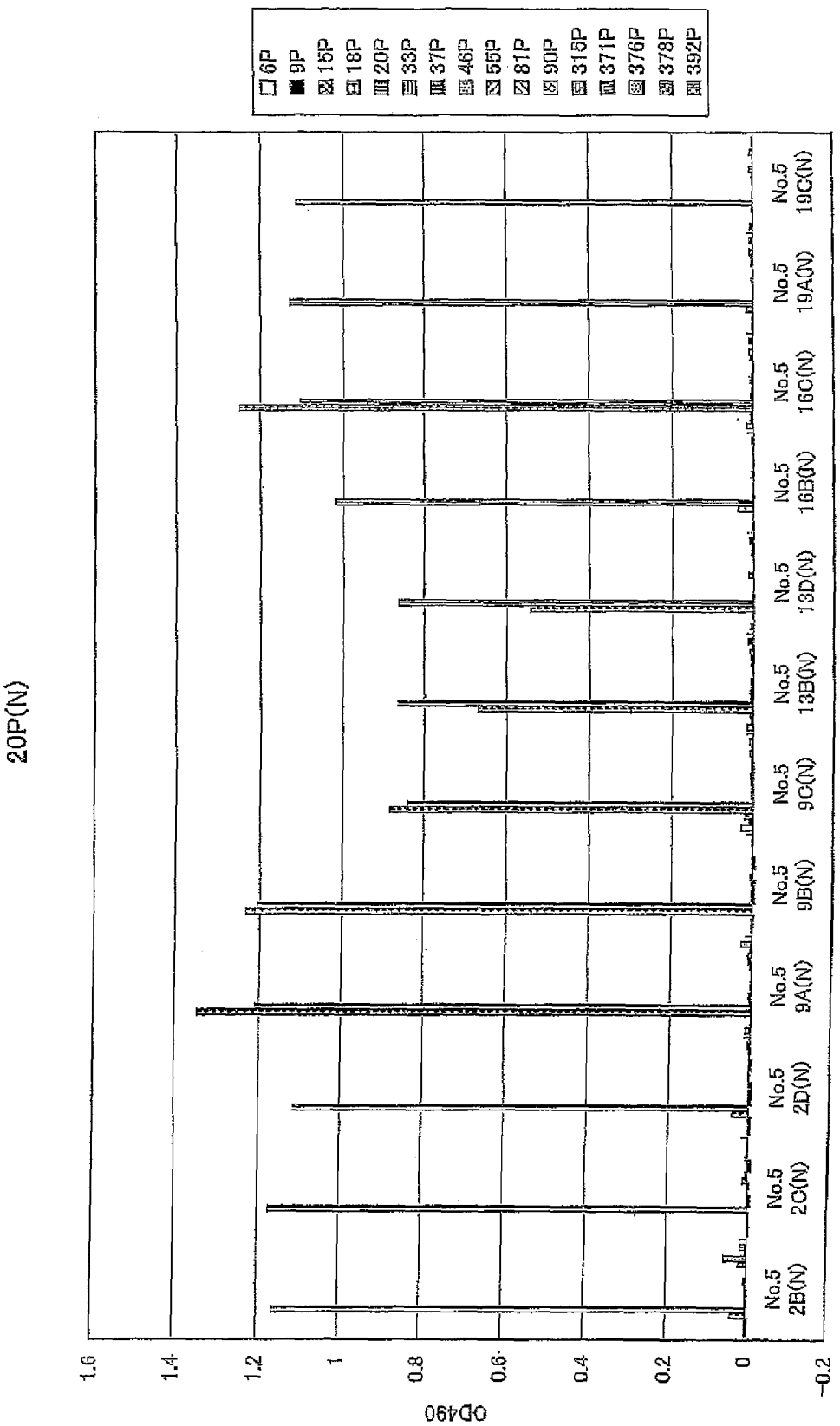
FIG. 7 is a graph showing results of crossreactivity with a monoclonal antibody.

FIG. 7 shows the results of crossreactivity of p53No. 5 2B(N) etc. with the peptides allowed to react with COSMEDIUM culture supernatant. As shown in FIG. 7, it was confirmed that p53No. 5 2B(N) etc. react specifically with phosphorylated modified Ser20.

Figure 8:
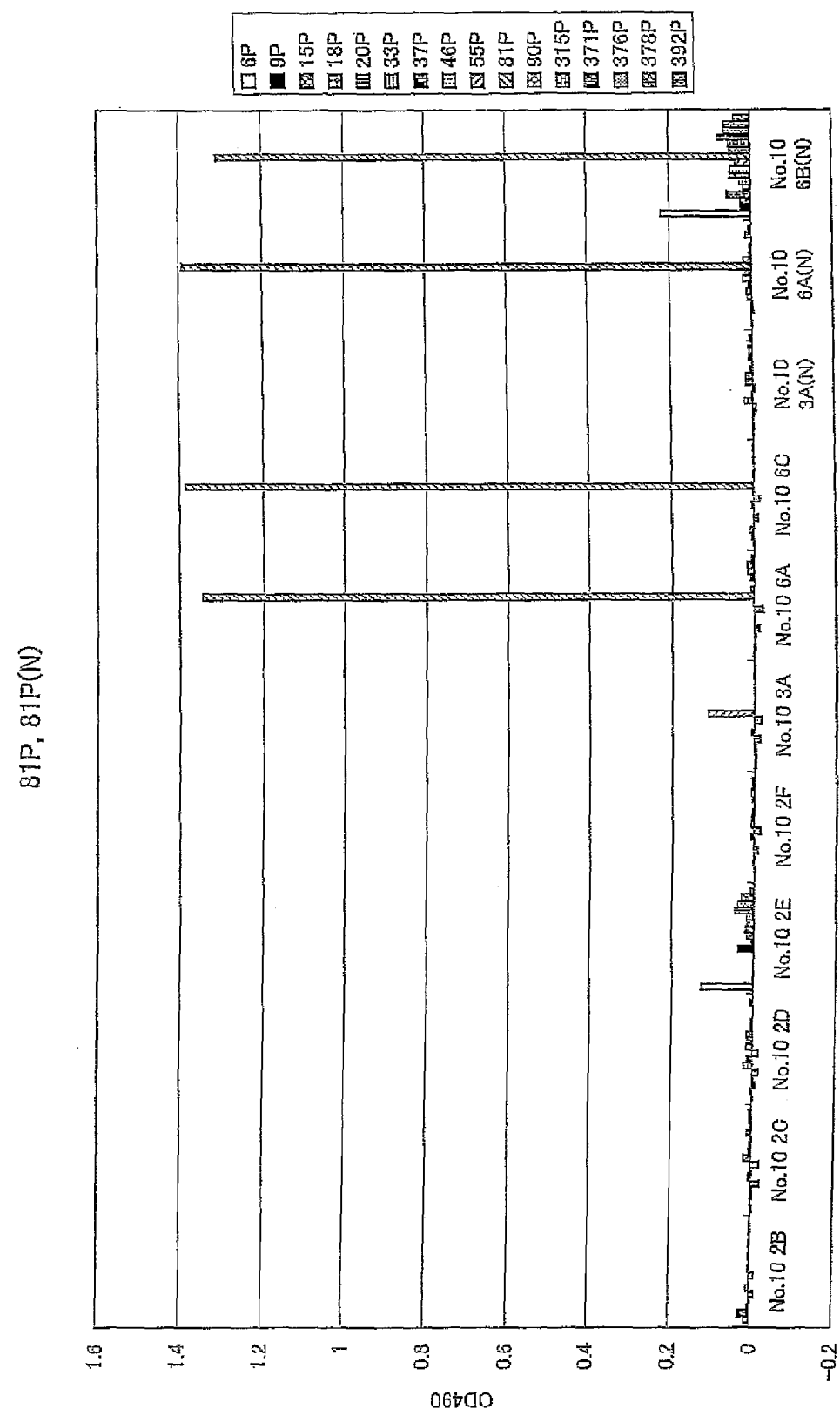
FIG. 8 is a graph showing results of crossreactivity with a monoclonal antibody.

As shown in FIG. 8, it was confirmed that p53No. 10 6A and p53No. 10 6C react specifically with phosphorylated modified Thr81. p53No. 10 6A(N) and p53No. 10 6B(N) were confirmed to react specifically with phosphorylated modified Thr81 even in the peptides allowed to react with COSMEDIUM culture supernatant.

Figure 9:
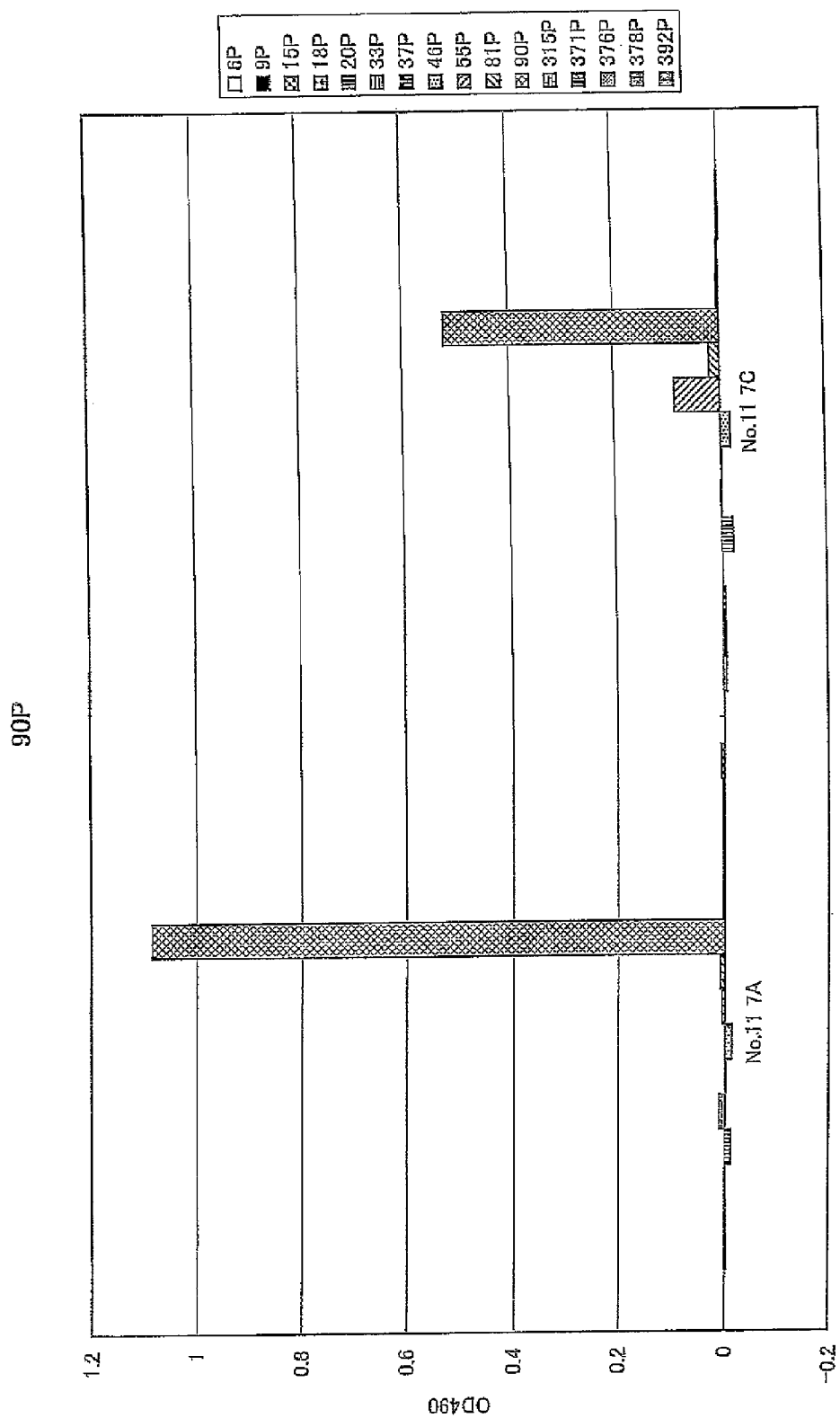
FIG. 9 is a graph showing results of crossreactivity with a monoclonal antibody.

As shown in FIG. 9, it was confirmed that p53No. 11 7A and p53No. 11 7C react specifically with phosphorylated modified Ser90.

Figure 10:
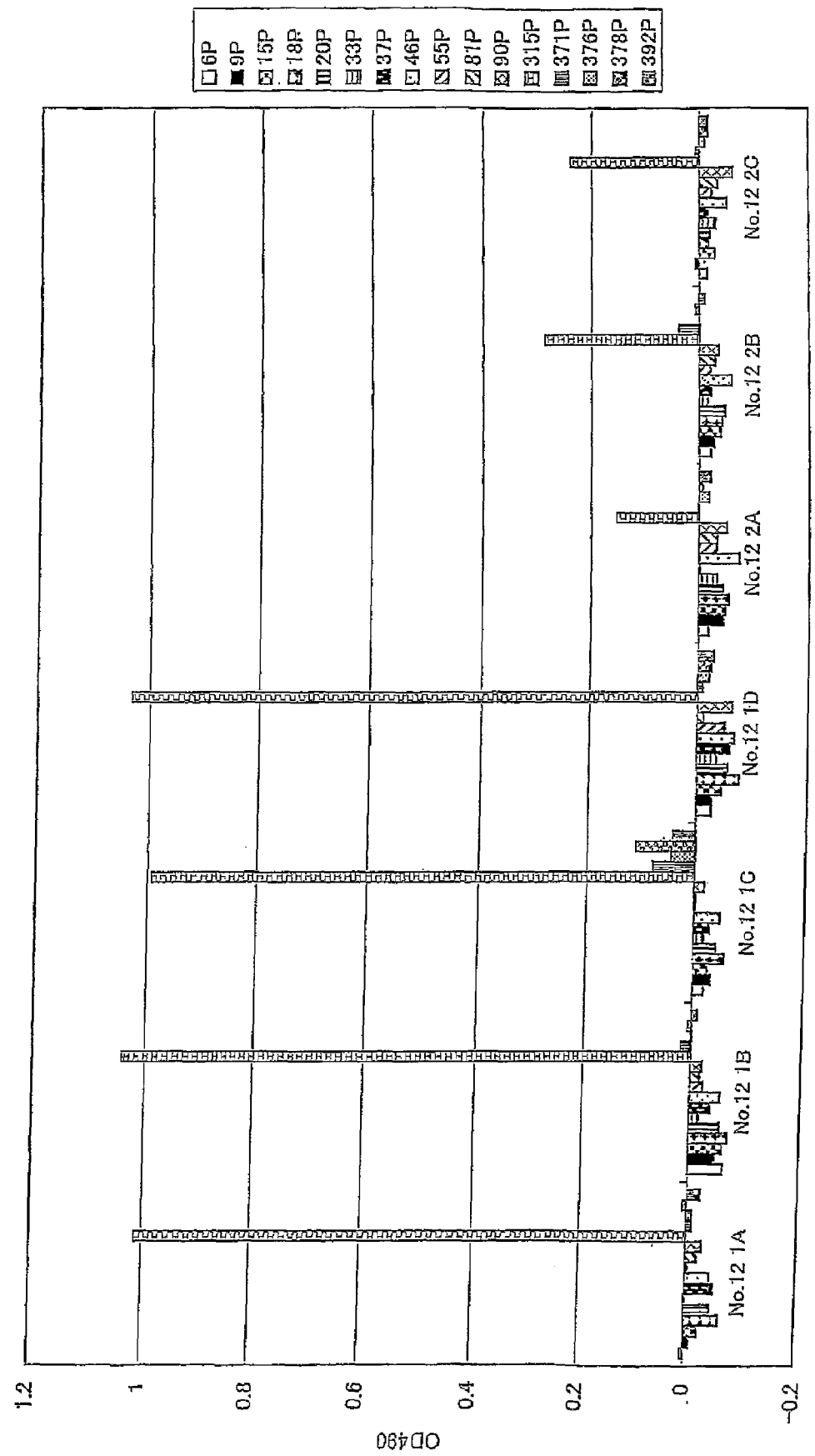
FIG. 10 is a graph showing results of crossreactivity with a monoclonal antibody.

As shown in FIG. 10, it was confirmed that p53No. 12 1A etc. react specifically with phosphorylated modified Ser315.

[Crossreactivity with the Acetylation-Recognizing Antibodies]

Figure 11:
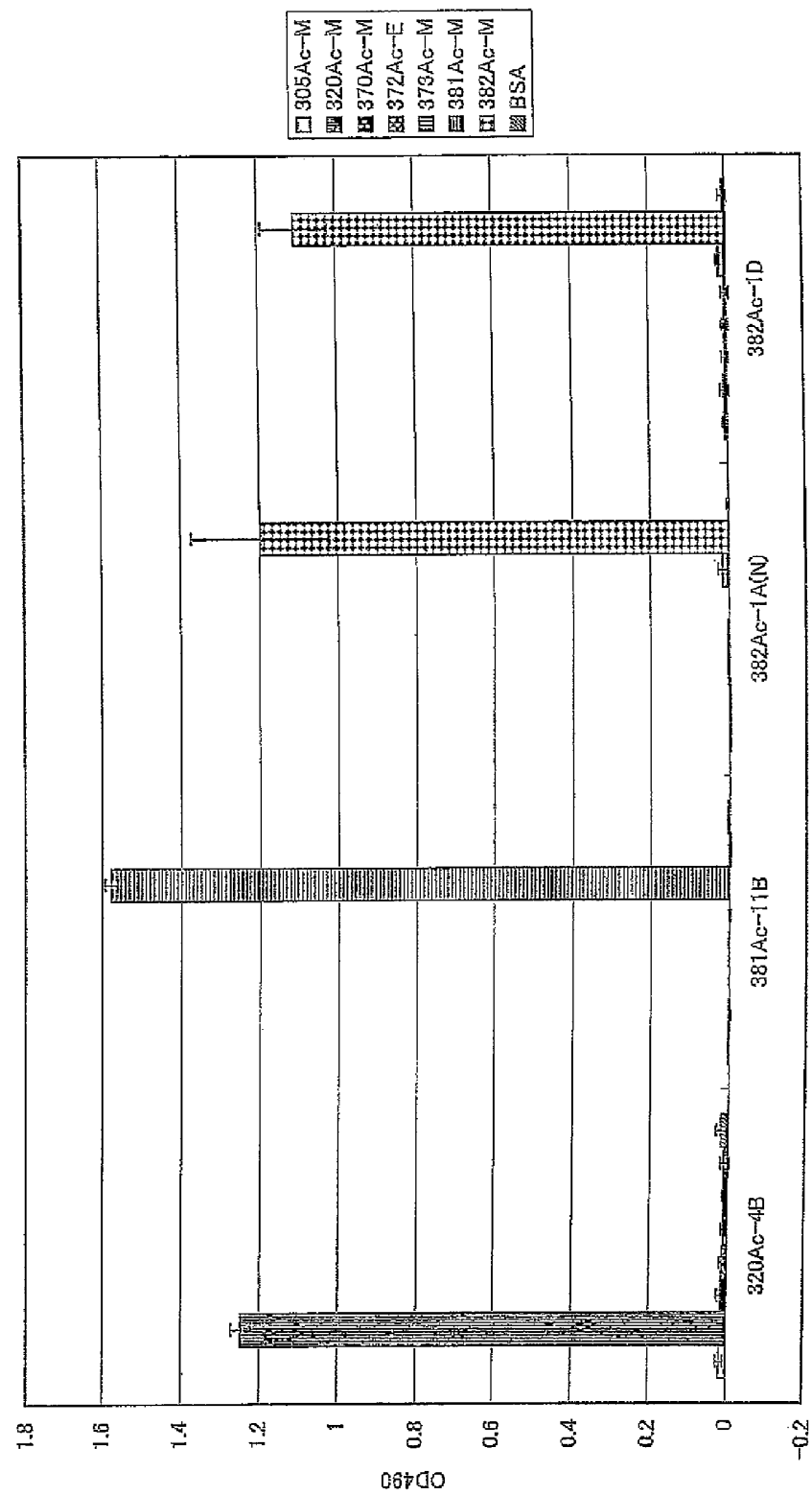
FIG. 11 is a graph showing results of crossreactivity with a monoclonal antibody.

1 µg/ml peptide of SEQ ID NO: 41, 42, 43, 90, 45, 46, or 47 (acetylated modified antigen peptide) in table 1, and bovine serum albumin (Product No. A7906, manufactured by Sigma) as the control, were pipetted respectively in a volume of 50 µl/well onto a 96-well immuno-plate (manufactured by NUNC) and then left overnight at room temperature, thereby coating the plate with the antigen peptide. Then, the solution was removed, each well was washed 5 times with a wash (TBS solution containing 0.1% Tween 20), and 200 µl TBS solution containing 4% BSA was added to each well and incubated at room temperature for 2 hours. After incubation, the solution was removed, each well was washed 5 times with a wash, and RPMI1640/10% FCS culture supernatant and COSMEDIUM culture supernatant (in the graph, (N) indicates COSMEDIUM culture supernatant) were added respectively in a volume of 45 µl to each well and incubated at room temperature for 2 hours. After incubation, the solution was removed, each well was washed 5 times with awash, and 40 µl dilution of HRP-bound goat anti-mouse IgG (Product No. NA931V, manufactured by Amersham Biosciences) prepared by diluting the IgG 5000-fold with a diluent (TBS solution containing 4% BSA and 0.1% Tween 20) was added to each well and incubated at room temperature for 30 minutes. After incubation, the solution was removed, the well was washed 5 times with a wash, and 100 µl substrate solution (o-phenylenediamine dihydrochloride (Sigma FAST) 50 set (Product No. P9187, manufactured by Sigma) was added to each well and reacted for 20 minutes. The coloration was terminated by adding 50 µl of 10% $H_2SO_4$, and each well was measured for absorbance at 490 nm with Microplate Reader Model 550 (manufactured by BIO-RAD). FIG. 11 shows the results of crossreactivity with the monoclonal antibodies. The absorbance at 490 nm is shown on the ordinate.

As shown in FIG. 11, it was confirmed that p53No. 18 4B specifically reacts with acetylated modified Lys320; p53No. 22 11B, with acetylated modified Lys381; and p58No. 23 1D, with acetylated modified Lys382. It was also confirmed that p53No. 23 1A(N) specifically reacts with acetylated modified Lys382 even in the peptides allowed to react with COSMEDIUM culture supernatant.

[Concentration Dependence of the Monoclonal Antibodies Acetylation-Recognizing Antibody Crossreactivity]

(p53No. 18 4B) 1 µg/ml peptide of each of SEQ ID NOS: 42 and 65 in table 1, and bovine serum albumin (Product No. A7906, manufactured by Sigma) as the control, were pipetted respectively in a volume of 50 μl/well onto a 96-well immuno-plate (manufactured by NUNC) and then left overnight at room temperature, thereby coating the plate with the antigen peptide. Then, the solution was removed, each well was washed 5 times with a wash (TBS solution containing 0.1% Tween 20), and 200 μl TBS solution containing 4% BSA was added to each well and incubated at room temperature for 2 hours. After incubation, the solution was removed, each well was washed 5 times with a wash, and 45 μl of RPMI1640/10% FCS culture supernatant was added to each well and incubated at room temperature for 2 hours. After incubation, the solution was removed, each well was washed 5 times with a wash, and 40 μl dilution of HRP-bound goat anti-mouse IgG (Product No. NA931V, manufactured by Amersham Biosciences) prepared by diluting the IgG 5000-fold with a diluent (TBS solution containing 4% BSA and 0.1% Tween 20) was added to each well and incubated at room temperature for 30 minutes. After incubation, the solution was removed, each well was washed 5 times with a wash, and 100 μl substrate solution (o-phenylenediamine dihydrochloride (Sigma FAST) 50 set (Product No. P9187, manufactured by Sigma) was added to each well and reacted for 20 minutes. The coloration was terminated by adding 50 μl of 10% $H_2SO_4$, and each well was measured for absorbance at 490 nm with Microplate Reader Model 550 (manufactured by BIO-RAD). The result is shown in FIG. 12.

Figure 12:
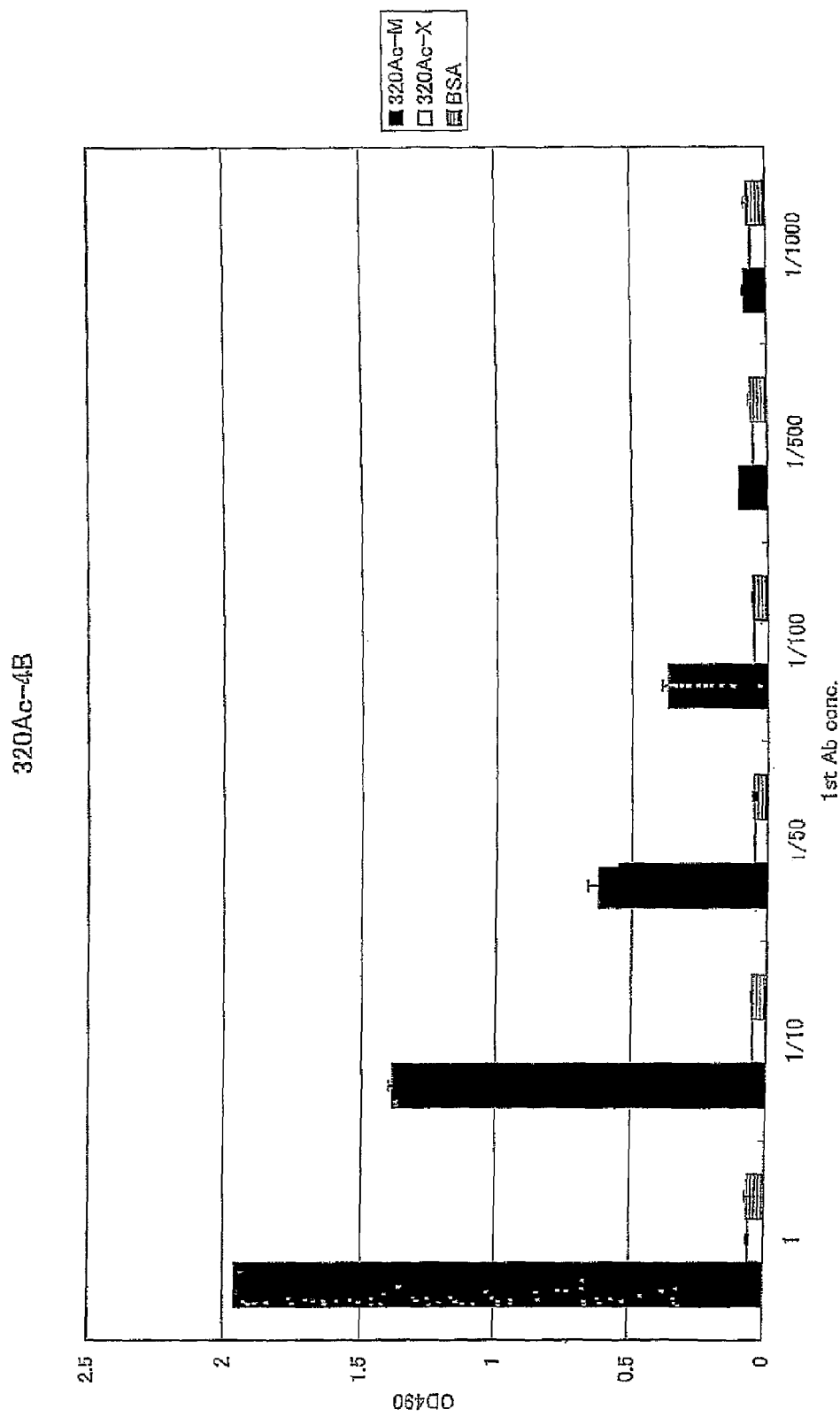
FIG. 12 is a graph showing the concentration dependence of a monoclonal antibody in acetylation-recognizing antibody crossreactivity.

As shown in FIG. 12, it was confirmed that p53No. 18 4B reacts specifically with the peptide of SEQ ID NO: 42 having acetylated modified Lys320 (as compared with the unmodified peptide (peptide of SEQ ID NO: 65)) and maintains specific reaction even if the concentration of p53No. 18 4B is decreased. It was confirmed that even if the concentration of the antibody is high, the antibody predominately recognizes acetylation.
(p53No. 23 1A)

1 μg/ml peptide of each of SEQ ID NOS: 47 and 70 in table 1, and bovine serum albumin (Product No. A7906, manufactured by Sigma) as the control, were pipetted respectively in a volume of 50 μl/well onto a 96-well immuno-plate (manufactured by NUNC) and then left overnight at room temperature, thereby coating the plate with the antigen peptide. Then, the solution was removed, each well was washed 5 times with a wash (TBS solution containing 0.1% Tween 20), and 200 μl TBS solution containing 4% BSA was added to each well and incubated at room temperature for 2 hours. After incubation, the solution was removed, each well was washed 5 times with a wash, and 45 μl of RPMI1640/10% FCS culture supernatant was added to each well and incubated at room temperature for 2 hours. After incubation, the solution was removed, each well was washed 5 times with a wash, and 40 μl dilution of HRP-bound goat anti-mouse IgG (Product No. NA931V, manufactured by Amersham Biosciences) prepared by diluting the IgG 5000-fold with a diluent (TBS solution containing 4% BSA and 0.1% Tween 20) was added to each well and incubated at room temperature for 30 minutes. After incubation, the solution was removed, each well was washed 5 times with a wash, and 100 μl substrate solution (o-phenylenediamine dihydrochloride (Sigma FAST) 50 set (Product No. P9187, manufactured by Sigma) was added to each well and reacted for 20 minutes. The coloration was terminated by adding 50 μl of 10% $H_2SO_4$, and each well was measured for absorbance at 490 nm with Microplate Reader Model 550 (manufactured by BIO-RAD). The result is shown in FIG. 13.

Figure 13:
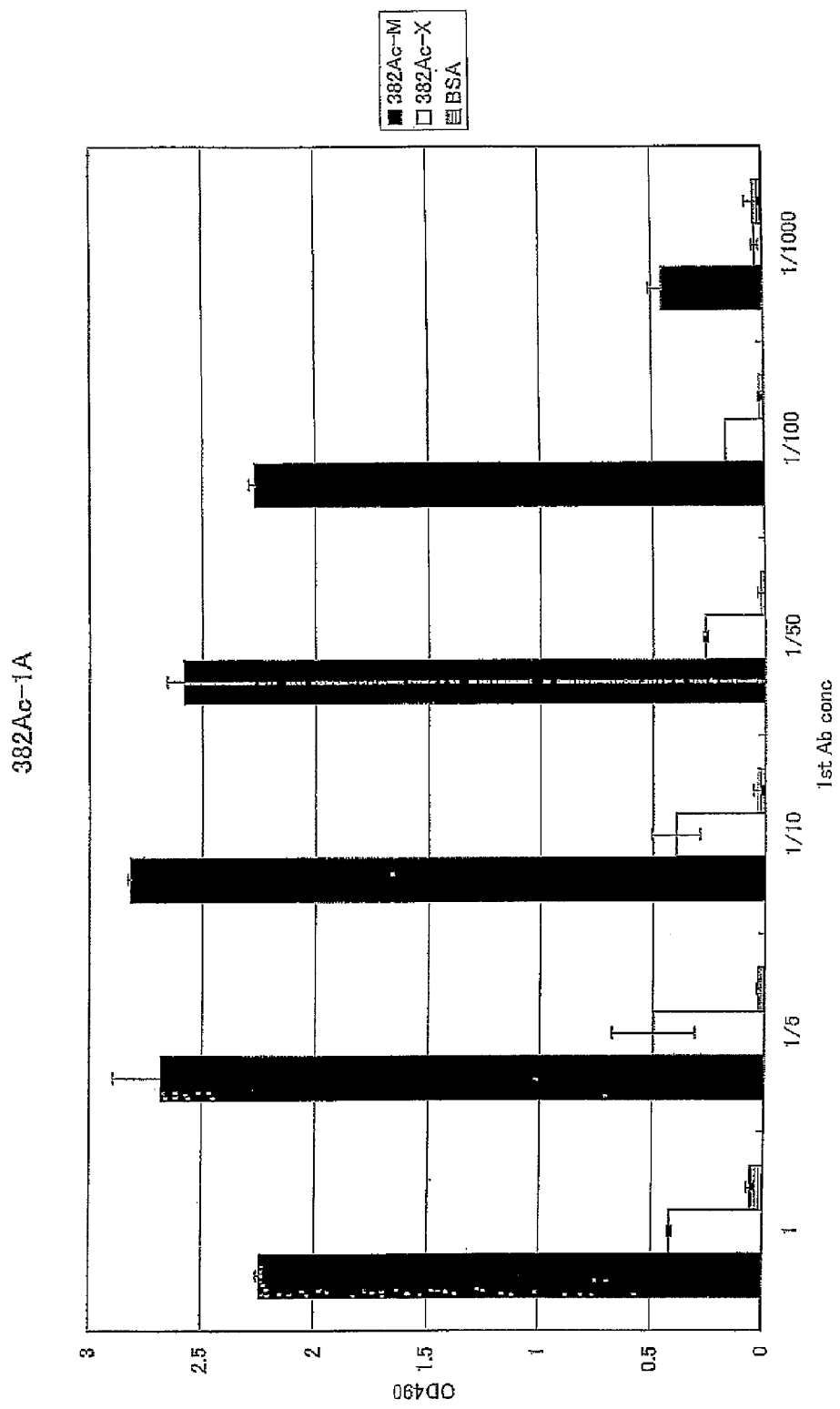
FIG. 13 is a graph showing the concentration dependence of a monoclonal antibody in acetylation-recognizing antibody crossreactivity.

As shown in FIG. 13, it was confirmed that p53No. 23 1A reacts specifically with the peptide of SEQ ID NO: 47 having acetylated modified Lys382 and maintains specific reaction even if the concentration of p53No. 23 1A is decreased. It was confirmed that even if the concentration of the antibody is high, the antibody predominately recognizes acetylation.
[Western Blotting]

Figure 14:
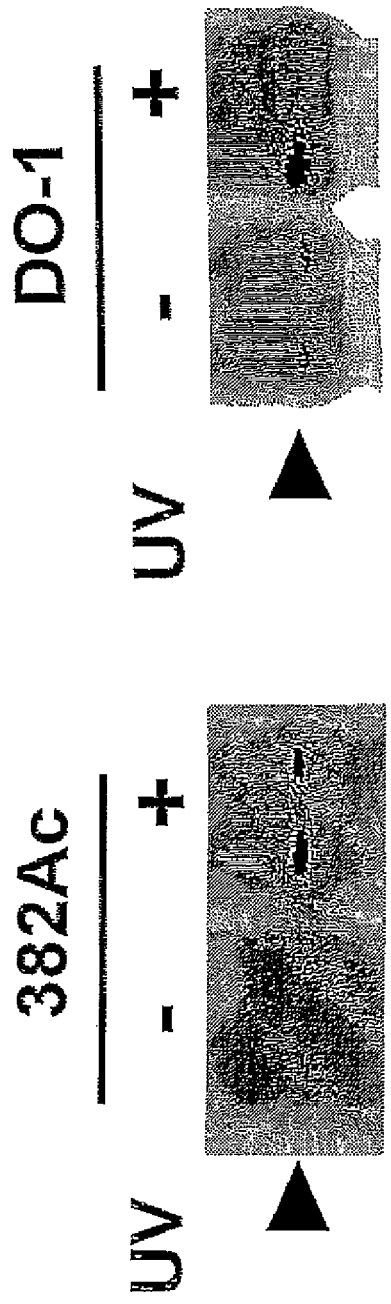
FIG. 14 shows results of Western blotting with 382Ac-1A antibody.

The results of Western blotting with 382Ac-1A antibody (p53No. 23 1A monoclonal antibody) are shown in FIG. 14. The experimental method is as follows: EGFP-p53R273H in H1299 cell (Product No. CRL5803, manufactured by ATCC) was irradiated with 25 J/m² (joule/square meter) ultra violet ray (UV), and after 24 hours, a cell extract containing p53 was recovered. When this cell extract was subjected to Western blotting with 382Ac-1A antibody, UV-dependent acetylation at 382 position in p53 could be detected as shown in FIG. 14. As the control, p53 DO-1 IgG2a antibody was used.

Reference Example 1

(1) Examination of Various Conditions in Preparation of the Antibody Microarray

Coating slide glass suitable for the antibody microarray of the present invention was examined. Slide glass examined is as follows: Coat for microarray for immobilization of X group-amino-modified oligodeoxyribonucleotide (manufactured by Matsunami Class Ind., Ltd.), Poly-L-Lysine Coat (manufactured by Matsunami Class Ind., Ltd.), a high-density amino group introduction-type coat (manufactured by Matsunami Class Ind., Ltd.), an epoxy group introduction-type coat (manufactured by Matsunami Class Ind., Ltd.), TYPE7 Slide (manufactured by Amersham), an aldehyde group introduction-type coat (manufactured by Matsunami Class Ind., Ltd.), TaKaRa-Hubble Slide Glass (Takara Bio), SMB Spot On™ DNA Slides (manufactured by Scandinavian Micro Biodevices A/S), Slide A (manufactured by SCHOTT), Geneslide 1 (manufactured by Toyo Kohan Co., Ltd.), Geneslide 2 (manufactured by Toyo Kohan Co., Ltd.), Immobilizer™ MicroArray slides (manufactured by EXIQON), CMT-GAPS (manufactured by Corning), Superchip C18 (manufactured by Corning), and Superchip C18-3D (manufactured by Corning) coating slide glass. p53 DO-1 IgG2a antibody (herein after referred to as "DO-1 antibody") was spotted at various concentrations (50, 100, 500, 1000 μg/ml) on each of the above coating slides, incubated for 3 hours and then blocked with 50 mM ethanolamine (pH 9.0). The detection was carried with Cy5-labeled IgG (42.5 nM). The reaction conditions were room temperature and 1 hour. FIG. 1 (in the figure, X refers to Coat for microarray for immobilization of X group-amino-modified oligodeoxyribonucleotide; 7-1, Poly-L-Lysine Coat; 7-3, epoxy group introduction-type coat; 7-5, TaKaRa-Hubble Slide Glass; 7-6, aldehyde group introduction-type coat; 7-7, SMB SpotOn™ DNA Slides; 7-9, geneslide 1; 7-10, geneslide 2; and 7-14, Immobilizer™ MicroArray slides) that all of the slides, Coat for microarray for immobilization of X group-amino-modified oligodeoxyribonucleotide could most stably detect the signal.

Reference Example 2

(2) Examination of State of Preservation of the Antibody Microarray

The protein may be deactivated when left in a dry state. Accordingly, storage conditions were examined to avoid a dry state. The following 3 conditions were examined.
1) After spotting and immobilization reaction, the protein is stored in PBS containing 40% glycerol and 0.1% $NaN_3$. After the slide is blocked, the protein is detected with a scanner.

2) After spotting and immobilization reaction, the protein is blocked and then stored in PBS containing 40% glycerol and 0.1% NaN₃, and then detected with a scanner.
3) After spotting and immobilization reaction, the protein is blocked and then detected with a scanner.

Figure 2:
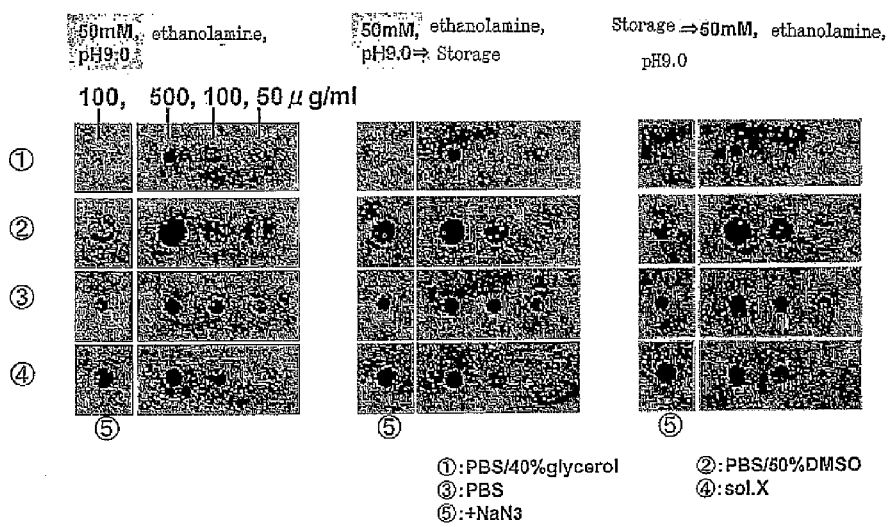
FIG. 2 shows spotted states of DO-1 antibody under various storage conditions.

As shown in FIG. 2, it was confirmed that in the case of spotting and subsequent immobilization reaction for 3 hours, spots flow when left in the preservation solution after spotting. However, it was revealed that by storage under the condition 2) above, the slide can be stored in an excellent state without flow of spots.

Reference Example 3

(3) Examination of Spotting Solution

A spotting solution most suitable for the coating slide glass was examined. DO-1 antibody in various spotting solutions (A: PBS/40% glycerol/0.1% NaN₃, B: PBS/50% DMSO/ 0.1% NaN₃, C: PBS/0.1% NaN₃, and D: Sol.X/0.1% NaN₃) was spotted, then immobilized/blocked, reacted with Cy5-labeled IgG, and detected with a scanner. For stability of the protein and for preventing volatilization of the protein-containing spotting solution, glycerol or DMSO should be added, but PBS/0.1% NaN₃ was most suitable.

Reference Example 4

(4) Examination of the Amount of the Antibodies Immobilized

Figure 3:
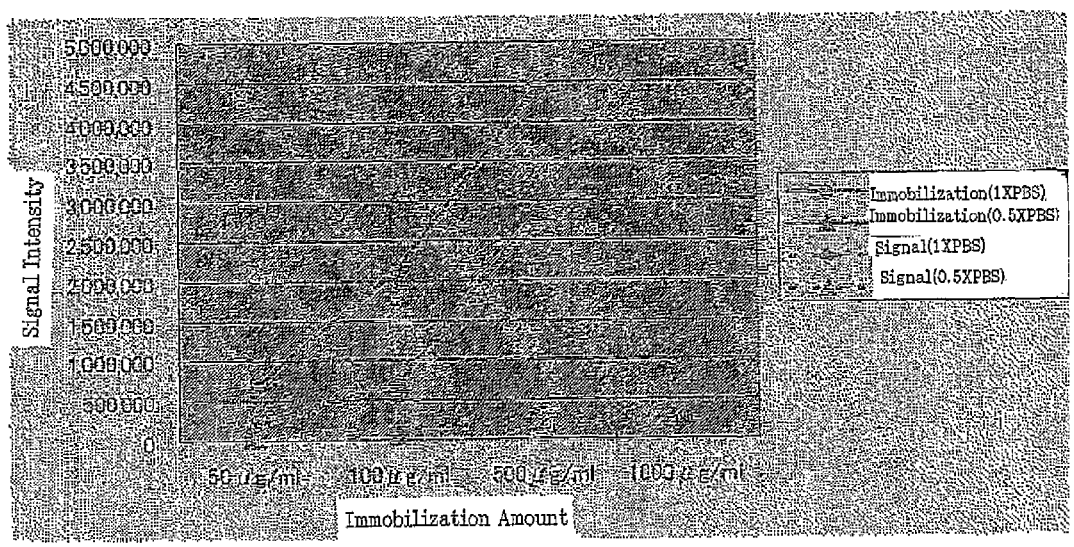
FIG. 3 is a graph showing the relationship between the amount of an antibody immobilized and the intensity of a signal.

50 μg/ml, 100 μg/ml, 500 μg/ml and 1000 μg/ml DO-1 antibody and 50 μg/ml, 100 μg/ml and 500 μg/ml Cy3-labeled DO-1 antibody were spotted on coating slide glass (Coat for microarray for immobilization of amino-modified oligodeoxyribonucleotide, manufactured by Matsunami Class Ind., Ltd.) and measured for their signal intensity and immobilization amount. As shown in FIG. 3, the immobilization amount is increased as the spotting amount is increased, but the immobilization amount for obtaining the signal was saturated at a concentration of 500 μg/ml, so it was found that the most suitable spotting amount is 500 μg/ml.

Reference Example 5

(5) Examination of Blocking Solution

Blocking suitable for slide glass coating was examined. An antibody microarray having Cy3-labeled DO-1 antibody immobilized thereon was blocked with a blocking solution (ethanolamine, glycine) and detected with a scanner (manufactured by Fuji Photo Film Co., Ltd.). Blocking was effected efficiently with either ethanolamine or glycine. From the viewpoint of preventing proteins from reacting with one another, ethanolamine is preferable as a blocking solution.

[Sequence Listing Free Text]

SEQ ID NOS: 2 to 17: (Phosphorylated) synthetic peptides
SEQ ID NOS: 18 to 24: (Acetylated) synthetic peptides
SEQ ID NOS: 25 to 40: (Phosphorylated) synthetic peptides
SEQ ID NOS: 41 to 47: (Acetylated) synthetic peptides
SEQ ID NOS: 48 to 70: (Unmodified) synthetic peptides
SEQ ID NOS: 71 to 86: (Phosphorylated) synthetic peptides
SEQ ID NOS: 87 to 93: (Acetylated) synthetic peptides

The invention claimed is:

1. A plurality of monoclonal antibodies for detecting the presence or absence of phosphorylation or acetylation of an amino acid residue in an amino acid sequence of SEQ ID NO: 1, said plurality comprising a monoclonal antibody produced by a hybridoma denoted by 53No. 5 16A (FERM ABP-10562).

2. The plurality of monoclonal antibodies according to claim 1, said plurality further comprising a monoclonal antibody that reacts specifically with: (a) a peptide comprising an amino acid sequence of at least 6 consecutive amino acids of SEQ ID NO:1, said peptide comprising a phosphorylated amino acid residue at position 15, position 18, position 81, position 90 or position 315, wherein the monoclonal antibody does not react with the peptide when it is not phosphorylated, or (b) a peptide comprising amino acid sequence of at least 6 consecutive amino acids of SEQ ID NO:1, said peptide comprising an acetylated amino acid residue at position 320, position 381 or position 382, wherein the monoclonal antibody does not react with the peptide when it is not acetylated.

3. The plurality of monoclonal antibodies according to claim 2, wherein a) said peptide comprising a phosphorylated amino acid residue at position 15 comprises SEQ ID NO: 4, wherein said peptide has reactivity with a monoclonal antibody produced by a hybridoma denoted by 53No. 3 3Bc (FERM ABP-10576); b) said peptide comprising a phosphorylated amino acid residue at position 18 comprises SEQ ID NO: 5, wherein said peptide has reactivity with a monoclonal antibody produced by a hybridoma denoted by 53No. 4 13C (FERM ABP-10577); c) said peptide comprising a phosphorylated amino acid residue at position 81 is SEQ ID NO: 11, wherein said peptide has reactivity with a monoclonal antibody produced by a hybridoma denoted by 53No. 10 6A (FERM ABP-10563); d) said peptide comprising a phosphorylated amino acid residue at position 90 comprises SEQ ID NO: 12 wherein said peptide has reactivity with a monoclonal antibody produced by a hybridoma denoted by 53No. 11 7C (FERM ABP-10578); or e) said peptide comprising a phosphorylated amino acid residue at position 315 comprises SEQ ID NO: 13, wherein said peptide has reactivity with a monoclonal antibody produced by a hybridoma denoted by 53No. 12 1A (FERM ABP-10579).

4. The plurality of monoclonal antibodies according to claim 2, wherein a) said peptide comprising an acetylated amino acid residue at position 320 comprises SEQ ID NO: 19, wherein said peptide has reactivity with a monoclonal antibody produced by a hybridoma denoted by 53No. 18 4B (FERM ABP-10561); b) said peptide comprising an acetylated amino acid residue at position 381 comprises SEQ ID NO: 23, wherein said peptide has reactivity with a monoclonal antibody produced by a hybridoma denoted by 53No. 22 11B (FERM ABP-10580); or c) said peptide comprising an acetylated amino acid residue at position 382 comprises SEQ ID NO: 24, wherein said peptide has reactivity with a monoclonal antibody produced by a hybridoma denoted by 53No. 23 1A (FERM ABP-10581).

5. The plurality of monoclonal antibodies according to claim 3, wherein said plurality of monoclonal antibodies further comprises a monoclonal antibody produced by a hybridoma denoted by: P53No. 3 3Bc (FERM ABP-10576), P53No. 4 13C (FERM ABP-10577), P53No. 10 6A (FERM ABP-10563), P53No. 11 7C (FERM ABP-10578), or P53No. 12 1A (FERM ABP-10579).

6. The plurality of monoclonal antibodies according to claim 4, wherein said plurality of monoclonal antibodies further comprises a monoclonal antibody produced by a hybridoma denoted by: P53No. 18 4B (FERM ABP-10561), P53No. 22 11B (FERM ABP-10580), or P53No. 23 1A (FERM ABP-10581).

7. A hybridoma denoted by: P53No. 3 3Bc (FERM ABP-10576), P53No. 4 13C (FERM ABP-10577), P53No. 5 16A (FERM ABP-10562), P53No. 10 6A (FERM ABP-10563), P53No. 11 7C (FERM ABP-10578), P53No. 12 1A (FERM ABP-10579), P53No. 18 4B (FERM ABP-10561), P53No. 22 11B (FERM ABP-10580), or P53No. 23 1A (FERM ABP-10581).

8. An antibody microarray comprising the plurality of monoclonal antibodies of claim 1 immobilized on a substrate.

9. A kit for measuring a modification state after translation of p53 protein, which comprises the plurality of monoclonal antibodies of claim 1.

10. A kit for measuring a modification state after translation of p53 protein, which comprises the antibody microarray according to claim 8.

11. A monoclonal antibody produced by a hybridoma denoted by P53No. 3 3Bc (FERM ABP-10576), P53No. 4 13C (FERM ABP-10577), P53No. 5 16A (FERM ABP-10562), P53No. 10 6A (FERM ABP-10563), P53No. 11 7C (FERM ABP-10578), P53No. 12 1A (FERM ABP-10579), P53No. 18 4B (FERM ABP-10561), P53No. 22 11B (FERM ABP-10580), or P53No. 23 1A (FERM ABP-10581).

12. A composition comprising the monoclonal antibody of claim 11.

13. A composition comprising the plurality of monoclonal antibodies according to claim 1.

14. A plurality of monoclonal antibodies according to claim 1, further comprising a monoclonal antibody produced by a hybridoma denoted by P53No. 3 3Bc (FERM ABP-10576), P53No. 4 13C (FERM ABP-10577), P53No. 10 6A (FERM ABP-10563), P53No. 11 7C (FERM ABP-10578), P53No. 12 1A (FERM ABP-10579), P53No. 18 4B (FERM ABP-10561), P53No. 22 11B (FERM ABP-10580), or P53No. 23 1A (FERM ABP-10581).

* * * * *

```
SEQUENCE LISTING

<160> NUMBER OF SEQ ID NOS: 93

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160
```

```
Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
            195                 200                 205

Arg Asn Thr Phe Arg His Ser Val Val Pro Tyr Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 2
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 2

Met Glu Glu Pro Gln Ser Asp Pro Ser Val Glu Pro
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 3

Pro Gln Ser Asp Pro Ser Val Glu Pro Pro Leu Ser
1               5                   10
```

```
<210> SEQ ID NO 4
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (5)..(5)
<223> OTHER INFORMATION: PHOSPHORYLATION

<400> SEQUENCE: 4

Glu Pro Pro Leu Ser Gln Glu Thr Phe Ser Asp Leu
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 5

Pro Leu Ser Gln Glu Thr Phe Ser Asp Leu Trp Lys
1               5                   10

<210> SEQ ID NO 6
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 6

Ser Gln Glu Thr Phe Ser Asp Leu Trp Lys Leu Leu
1               5                   10

<210> SEQ ID NO 7
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 7

Pro Glu Asn Asn Val Leu Ser Pro Leu Pro Ser Gln Ala
1               5                   10

<210> SEQ ID NO 8
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION
```

```
<400> SEQUENCE: 8

Leu Ser Pro Leu Pro Ser Gln Ala Met Asp Asp Leu
1               5                   10

<210> SEQ ID NO 9
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 9

Asp Asp Leu Met Leu Ser Pro Asp Asp Ile Glu Gln
1               5                   10

<210> SEQ ID NO 10
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 10

Ile Glu Gln Trp Phe Thr Glu Asp Pro Gly Pro Asp
1               5                   10

<210> SEQ ID NO 11
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 11

Ala Pro Ala Ala Pro Thr Pro Ala Ala Pro Ala Pro
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 12

Pro Ala Pro Ala Pro Ser Trp Pro Leu Ser Ser Ser
1               5                   10

<210> SEQ ID NO 13
<211> LENGTH: 12
<212> TYPE: PRT
<213> ORGANISM: Artificial sequence
<220> FEATURE:
<223> OTHER INFORMATION: Synthesized peptide (phosphorylated)
```

```
<220> FEATURE:
<221> NAME/KEY: MOD_RES
<222> LOCATION: (6)..(6)
<223> OTHER INFORMATION: PHOSPHORYLATION

<400> SEQUENCE: 13

Asn Asn Thr Ser Ser Ser Pro Gln Pro Lys Lys Lys
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 14

Ser Ser His Leu Lys Ser Lys Lys Gly Gln Ser Thr
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 15

Ser Lys Lys Gly Gln Ser Thr Ser Arg His Lys Lys
1               5                   10

<210> SEQ ID NO 16
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 16

Lys Lys Gly Gln Ser Thr Ser Arg His Lys Lys Leu Met Phe
1               5                   10

<210> SEQ ID NO 17
<211> LENGTH: 9
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (8)..(8)
<223> OTHER INFORMATION: PHOSPHORYLATION

<400> SEQUENCE: 17

Phe Lys Thr Glu Gly Pro Asp Ser Asp
1               5

<210> SEQ ID NO 18
```

```
<211> LENGTH: 12
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 18

Pro Pro Gly Ser Thr Lys Arg Ala Leu Pro Asn Asn
1               5                   10

<210> SEQ ID NO 19
<211> LENGTH: 11
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 19

Ser Pro Gln Pro Lys Lys Lys Pro Leu Asp Gly
1               5                   10

<210> SEQ ID NO 20
<211> LENGTH: 11
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 20

His Ser Ser His Leu Lys Ser Lys Lys Gly Gln
1               5                   10

<210> SEQ ID NO 21
<211> LENGTH: 11
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 21

Ser His Leu Lys Ser Lys Lys Gly Gln Ser Thr
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 22
```

```
His Leu Lys Ser Lys Lys Gly Gln Ser Thr Ser
1               5                   10
```

```
<210> SEQ ID NO 23
<211> LENGTH: 11
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 23

Ser Thr Ser Arg His Lys Lys Leu Met Phe Lys
1               5                   10
```

```
<210> SEQ ID NO 24
<211> LENGTH: 11
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 24

Thr Ser Arg His Lys Lys Leu Met Phe Lys Thr
1               5                   10
```

```
<210> SEQ ID NO 25
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION (Phosphoserine)

<400> SEQUENCE: 25

Met Glu Glu Pro Gln Ser Asp Pro Ser Val Glu Pro Cys
1               5                   10
```

```
<210> SEQ ID NO 26
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION (Phosphoserine)

<400> SEQUENCE: 26

Pro Gln Ser Asp Pro Ser Val Glu Pro Pro Leu Ser Cys
1               5                   10
```

```
<210> SEQ ID NO 27
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
```

```
<222> LOCATION: (5)..(5)
<223> OTHER INFORMATION: PHOSPHORYLATION (Phosphoserine)

<400> SEQUENCE: 27

Glu Pro Pro Leu Ser Gln Glu Thr Phe Ser Asp Leu Cys
1               5                   10

<210> SEQ ID NO 28
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION (Phosphothreonine)

<400> SEQUENCE: 28

Pro Leu Ser Gln Glu Thr Phe Ser Asp Leu Trp Lys Cys
1               5                   10

<210> SEQ ID NO 29
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION (Phosphoserine)

<400> SEQUENCE: 29

Ser Gln Glu Thr Phe Ser Asp Leu Trp Lys Leu Leu Cys
1               5                   10

<210> SEQ ID NO 30
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 30

Pro Glu Asn Asn Val Leu Ser Pro Leu Pro Ser Gln Ala Cys
1               5                   10

<210> SEQ ID NO 31
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 31

Leu Ser Pro Leu Pro Ser Gln Ala Met Asp Asp Leu Cys
1               5                   10

<210> SEQ ID NO 32
<211> LENGTH: 13
<212> TYPE: PRT
```

```
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 32

Asp Asp Leu Met Leu Ser Pro Asp Asp Ile Glu Gln Cys
1               5                   10

<210> SEQ ID NO 33
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 33

Ile Glu Gln Trp Phe Thr Glu Asp Pro Gly Pro Asp Cys
1               5                   10

<210> SEQ ID NO 34
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 34

Ala Pro Ala Ala Pro Thr Pro Ala Ala Pro Ala Pro Cys
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 35

Pro Ala Pro Ala Pro Ser Trp Pro Leu Ser Ser Ser Cys
1               5                   10

<210> SEQ ID NO 36
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 36

Asn Asn Thr Ser Ser Ser Pro Gln Pro Lys Lys Lys Cys
1               5                   10
```

```
<210> SEQ ID NO 37
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 37

Ser Ser His Leu Lys Ser Lys Lys Gly Gln Ser Thr Cys
1               5                   10

<210> SEQ ID NO 38
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 38

Ser Lys Lys Gly Gln Ser Thr Ser Arg His Lys Lys Cys
1               5                   10

<210> SEQ ID NO 39
<211> LENGTH: 15
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (8)..(8)
<223> OTHER INFORMATION: PHOSPHORYLATION

<400> SEQUENCE: 39

Cys Lys Lys Gly Gln Ser Thr Ser Arg His Lys Lys Leu Met Phe
1               5                   10                  15

<210> SEQ ID NO 40
<211> LENGTH: 10
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (9)..(9)
<223> OTHER INFORMATION: PHOSPHORYLATION

<400> SEQUENCE: 40

Cys Phe Lys Thr Glu Gly Pro Asp Ser Asp
1               5                   10

<210> SEQ ID NO 41
<211> LENGTH: 13
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION
```

```
<400> SEQUENCE: 41

Pro Pro Gly Ser Thr Lys Arg Ala Leu Pro Asn Asn Cys
1               5                   10

<210> SEQ ID NO 42
<211> LENGTH: 12
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 42

Ser Pro Gln Pro Lys Lys Lys Pro Leu Asp Gly Cys
1               5                   10

<210> SEQ ID NO 43
<211> LENGTH: 12
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 43

His Ser Ser His Leu Lys Ser Lys Lys Gly Gln Cys
1               5                   10

<210> SEQ ID NO 44
<211> LENGTH: 12
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 44

Ser His Leu Lys Ser Lys Lys Gly Gln Ser Thr Cys
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 45

His Leu Lys Ser Lys Lys Gly Gln Ser Thr Ser Cys
1               5                   10

<210> SEQ ID NO 46
<211> LENGTH: 12
<212> TYPE: PRT
<213> ORGANISM: Artificial sequence
<220> FEATURE:
```

```
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 46

Ser Thr Ser Arg His Lys Lys Leu Met Phe Lys Cys
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (6)..(6)
<223> OTHER INFORMATION: ACETYLATION

<400> SEQUENCE: 47

Thr Ser Arg His Lys Lys Leu Met Phe Lys Thr Cys
1               5                   10

<210> SEQ ID NO 48
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 48

Met Glu Glu Pro Gln Ser Asp Pro Ser Val Glu Pro Cys
1               5                   10

<210> SEQ ID NO 49
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 49

Pro Gln Ser Asp Pro Ser Val Glu Pro Pro Leu Ser Cys
1               5                   10

<210> SEQ ID NO 50
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 50

Glu Pro Pro Leu Ser Gln Glu Thr Phe Ser Asp Leu Cys
1               5                   10

<210> SEQ ID NO 51
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 51

Pro Leu Ser Gln Glu Thr Phe Ser Asp Leu Trp Lys Cys
1               5                   10
```

```
<210> SEQ ID NO 52
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 52

Ser Gln Glu Thr Phe Ser Asp Leu Trp Lys Leu Leu Cys
1               5                   10

<210> SEQ ID NO 53
<211> LENGTH: 14
<212> TYPE: PRT
<213> ORGANISM: Artificial sequence
<220> FEATURE:
<223> OTHER INFORMATION: Synthesized peptide (unmodified)

<400> SEQUENCE: 53

Pro Glu Asn Asn Val Leu Ser Pro Leu Pro Ser Gln Ala Cys
1               5                   10

<210> SEQ ID NO 54
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 54

Leu Ser Pro Leu Pro Ser Gln Ala Met Asp Asp Leu Cys
1               5                   10

<210> SEQ ID NO 55
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 55

Asp Asp Leu Met Leu Ser Pro Asp Asp Ile Glu Gln Cys
1               5                   10

<210> SEQ ID NO 56
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 56

Ile Glu Gln Trp Phe Thr Glu Asp Pro Gly Pro Asp Cys
1               5                   10

<210> SEQ ID NO 57
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 57

Ala Pro Ala Ala Pro Thr Pro Ala Ala Pro Ala Pro Cys
1               5                   10

<210> SEQ ID NO 58
```

```
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 58

Pro Ala Pro Ala Pro Ser Trp Pro Leu Ser Ser Ser Cys
1               5                   10

<210> SEQ ID NO 59
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 59

Asn Asn Thr Ser Ser Ser Pro Gln Pro Lys Lys Lys Cys
1               5                   10

<210> SEQ ID NO 60
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 60

Ser Ser His Leu Lys Ser Lys Lys Gly Gln Ser Thr Cys
1               5                   10

<210> SEQ ID NO 61
<211> LENGTH: 13
<212> TYPE: PRT
<213> ORGANISM: Artificial sequence
<220> FEATURE:
<223> OTHER INFORMATION: Synthesized peptide (unmodified)

<400> SEQUENCE: 61

Ser Lys Lys Gly Gln Ser Thr Ser Arg His Lys Lys Cys
1               5                   10

<210> SEQ ID NO 62
<211> LENGTH: 15
<212> TYPE: PRT
<213> ORGANISM: Artificial sequence
<220> FEATURE:
<223> OTHER INFORMATION: Synthesized peptide (unmodified)

<400> SEQUENCE: 62

Cys Lys Lys Gly Gln Ser Thr Ser Arg His Lys Lys Leu Met Phe
1               5                   10                  15

<210> SEQ ID NO 63
<211> LENGTH: 10
<212> TYPE: PRT
<213> ORGANISM: Artificial sequence
<220> FEATURE:
<223> OTHER INFORMATION: Synthesized peptide (unmodified)

<400> SEQUENCE: 63

Cys Phe Lys Thr Glu Gly Pro Asp Ser Asp
1               5                   10

<210> SEQ ID NO 64
<211> LENGTH: 13
<212> TYPE: PRT
```

```
<213> ORGANISM: Artificial sequence
<220> FEATURE:
<223> OTHER INFORMATION: Synthesized peptide (unmodified)

<400> SEQUENCE: 64

Pro Pro Gly Ser Thr Lys Arg Ala Leu Pro Asn Asn Cys
1               5                   10

<210> SEQ ID NO 65
<211> LENGTH: 12
<212> TYPE: PRT
<213> ORGANISM: Artificial sequence
<220> FEATURE:
<223> OTHER INFORMATION: Synthesized peptide (unmodified)

<400> SEQUENCE: 65

Ser Pro Gln Pro Lys Lys Lys Pro Leu Asp Gly Cys
1               5                   10

<210> SEQ ID NO 66
<211> LENGTH: 12
<212> TYPE: PRT
<213> ORGANISM: Artificial sequence
<220> FEATURE:
<223> OTHER INFORMATION: Synthesized peptide (unmodified)

<400> SEQUENCE: 66

His Ser Ser His Leu Lys Ser Lys Lys Gly Gln Cys
1               5                   10

<210> SEQ ID NO 67
<211> LENGTH: 12
<212> TYPE: PRT
<213> ORGANISM: Artificial sequence
<220> FEATURE:
<223> OTHER INFORMATION: Synthesized peptide (unmodified)

<400> SEQUENCE: 67

Ser His Leu Lys Ser Lys Lys Gly Gln Ser Thr Cys
1               5                   10

<210> SEQ ID NO 68
<211> LENGTH: 12
<212> TYPE: PRT
<213> ORGANISM: Artificial sequence
<220> FEATURE:
<223> OTHER INFORMATION: Synthesized peptide (unmodified)

<400> SEQUENCE: 68

His Leu Lys Ser Lys Lys Gly Gln Ser Thr Ser Cys
1               5                   10

<210> SEQ ID NO 69
<211> LENGTH: 12
<212> TYPE: PRT
<213> ORGANISM: Artificial sequence
<220> FEATURE:
<223> OTHER INFORMATION: Synthesized peptide (unmodified)

<400> SEQUENCE: 69

Ser Thr Ser Arg His Lys Lys Leu Met Phe Lys Cys
1               5                   10

<210> SEQ ID NO 70
<211> LENGTH: 12
<212> TYPE: PRT
<213> ORGANISM: Artificial sequence
<220> FEATURE:
```

<223> OTHER INFORMATION: Synthesized peptide (unmodified)

<400> SEQUENCE: 70

Thr Ser Arg His Lys Lys Leu Met Phe Lys Thr Cys
1               5                   10

<210> SEQ ID NO 71
<211> LENGTH: 13
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 71

Met Glu Glu Pro Gln Ser Asp Pro Ser Val Glu Pro Cys
1               5                   10

<210> SEQ ID NO 72
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 72

Glu Pro Gln Ser Asp Pro Ser Val Glu Pro Pro Leu Ser Cys
1               5                   10

<210> SEQ ID NO 73
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (6)..(6)
<223> OTHER INFORMATION: PHOSPHORYLATION

<400> SEQUENCE: 73

Val Glu Pro Pro Leu Ser Gln Glu Thr Phe Ser Asp Leu Cys
1               5                   10

<210> SEQ ID NO 74
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 74

Pro Pro Leu Ser Gln Glu Thr Phe Ser Asp Leu Trp Lys Cys
1               5                   10

<210> SEQ ID NO 75
<211> LENGTH: 14
<212> TYPE: PRT
<213> ORGANISM: Artificial sequence

```
-continued

<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 75

Leu Ser Gln Glu Thr Phe Ser Asp Leu Trp Lys Leu Leu Cys
1               5                   10

<210> SEQ ID NO 76
<211> LENGTH: 15
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (8)..(8)
<223> OTHER INFORMATION: PHOSPHORYLATION

<400> SEQUENCE: 76

Leu Pro Glu Asn Asn Val Leu Ser Pro Leu Pro Ser Gln Ala Cys
1               5                   10                  15

<210> SEQ ID NO 77
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: Phosphorylation
<222> LOCATION: (7)..(7)
<223> OTHER INFORMATION:
<220> FEATURE:
<221> NAME/KEY: MOD_RES
<222> LOCATION: (7)..(7)
<223> OTHER INFORMATION: PHOSPHORYLATION

<400> SEQUENCE: 77

Val Leu Ser Pro Leu Pro Ser Gln Ala Met Asp Asp Leu Cys
1               5                   10

<210> SEQ ID NO 78
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 78

Met Asp Asp Leu Met Leu Ser Pro Asp Asp Ile Glu Gln Cys
1               5                   10

<210> SEQ ID NO 79
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 79
```

```
Asp Ile Glu Gln Trp Phe Thr Glu Asp Pro Gly Pro Asp Cys
1               5                   10

<210> SEQ ID NO 80
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 80

Pro Ala Pro Ala Ala Pro Thr Pro Ala Ala Pro Ala Pro Cys
1               5                   10

<210> SEQ ID NO 81
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 81

Ala Pro Ala Pro Ala Pro Ser Trp Pro Leu Ser Ser Ser Cys
1               5                   10

<210> SEQ ID NO 82
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 82

Pro Asn Asn Thr Ser Ser Ser Pro Gln Pro Lys Lys Lys Cys
1               5                   10

<210> SEQ ID NO 83
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (7)..(7)
<223> OTHER INFORMATION: PHOSPHORYLATION

<400> SEQUENCE: 83

His Ser Ser His Leu Lys Ser Lys Lys Gly Gln Ser Thr Cys
1               5                   10

<210> SEQ ID NO 84
<211> LENGTH: 14
<212> TYPE: PRT
<213> ORGANISM: Artificial sequence
<220> FEATURE:
<223> OTHER INFORMATION: Synthesized peptide (phosphorylated)
<220> FEATURE:
```

```
<221> NAME/KEY: MOD_RES
<222> LOCATION: (7)..(7)
<223> OTHER INFORMATION: PHOSPHORYLATION

<400> SEQUENCE: 84

Lys Ser Lys Lys Gly Gln Ser Thr Ser Arg His Lys Lys Cys
1               5                   10

<210> SEQ ID NO 85
<211> LENGTH: 15
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (8)..(8)
<223> OTHER INFORMATION: PHOSPHORYLATION

<400> SEQUENCE: 85

Ser Lys Lys Gly Gln Ser Thr Ser Arg His Lys Lys Leu Met Phe
1               5                   10                  15

<210> SEQ ID NO 86
<211> LENGTH: 10
<212> TYPE: PRT
<213> ORGANISM: Artificial sequence
<220> FEATURE:
<223> OTHER INFORMATION: Synthesized peptide (phosphorylated)
<220> FEATURE:
<221> NAME/KEY: MOD_RES
<222> LOCATION: (9)..(9)
<223> OTHER INFORMATION: PHOSPHORYLATION

<400> SEQUENCE: 86

Met Phe Lys Thr Glu Gly Pro Asp Ser Asp
1               5                   10

<210> SEQ ID NO 87
<211> LENGTH: 14
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION

<400> SEQUENCE: 87

Leu Pro Pro Gly Ser Thr Lys Arg Ala Leu Pro Asn Asn Cys
1               5                   10

<210> SEQ ID NO 88
<211> LENGTH: 13
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION

<400> SEQUENCE: 88

Ser Ser Pro Gln Pro Lys Lys Pro Leu Asp Gly Cys
1               5                   10

<210> SEQ ID NO 89
<211> LENGTH: 13
```

```
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION

<400> SEQUENCE: 89

Ala His Ser Ser His Leu Lys Ser Lys Lys Gly Gln Cys
1               5                   10

<210> SEQ ID NO 90
<211> LENGTH: 13
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION

<400> SEQUENCE: 90

Ser Ser His Leu Lys Ser Lys Lys Gly Gln Ser Thr Cys
1               5                   10

<210> SEQ ID NO 91
<211> LENGTH: 13
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION

<400> SEQUENCE: 91

Ser His Leu Lys Ser Lys Lys Gly Gln Ser Thr Ser Cys
1               5                   10

<210> SEQ ID NO 92
<211> LENGTH: 13
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION

<400> SEQUENCE: 92

Gln Ser Thr Ser Arg His Lys Lys Leu Met Phe Lys Cys
1               5                   10

<210> SEQ ID NO 93
<211> LENGTH: 13
<212> TYPE: PRT
<213> ORGANISM: Artificial sequence
<220> FEATURE:
<223> OTHER INFORMATION: Synthesized peptide (acetylated)
<220> FEATURE:
<221> NAME/KEY: MOD_RES
<222> LOCATION: (7)..(7)
<223> OTHER INFORMATION: ACETYLATION
```

<400> SEQUENCE: 93

Ser Thr Ser Arg His Lys Lys Leu Met Phe Lys Thr Cys
1               5                   10